United States Patent
Nicolaou et al.

(10) Patent No.: US 6,904,423 B1
(45) Date of Patent: Jun. 7, 2005

(54) METHOD AND SYSTEM FOR ARTIFICIAL INTELLIGENCE DIRECTED LEAD DISCOVERY THROUGH MULTI-DOMAIN CLUSTERING

(75) Inventors: Christodoulos A. Nicolaou, Limassol (CY); Brian P. Kelley, Santa Fe, NM (US); Ruth F. Nutt, Santa Fe, NM (US); Susan I. Bassett, Santa Fe, NM (US)

(73) Assignee: Bioreason, Inc., Santa Fe, NM (US)

( * ) Notice: Subject to any disclaimer, the term of this patent is extended or adjusted under 35 U.S.C. 154(b) by 0 days.

(21) Appl. No.: 09/506,948

(22) Filed: Feb. 18, 2000

Related U.S. Application Data

(60) Provisional application No. 60/120,701, filed on Feb. 19, 1999.

(51) Int. Cl.$^7$ .................................................. G06N 7/00
(52) U.S. Cl. ......................................... 706/46; 702/22
(58) Field of Search .......................... 702/22; 422/186; 715/532; 706/46

(56) References Cited

U.S. PATENT DOCUMENTS

| | | | |
|---|---|---|---|
| 5,025,388 A | | 6/1991 | Cramer, III et al. |
| 5,263,120 A | | 11/1993 | Bickel |
| 5,307,287 A | | 4/1994 | Cramer, III et al. |
| 5,590,218 A | | 12/1996 | Ornstein ..................... 382/157 |
| 5,619,709 A | * | 4/1997 | Caid et al. ................... 715/532 |
| 5,684,711 A | | 11/1997 | Agrafiotis et al. |
| 5,751,605 A | | 5/1998 | Hurst et al. |
| 5,825,909 A | * | 10/1998 | Jang ............................ 382/132 |
| 6,182,016 B1 | * | 1/2001 | Liang et al. ................... 702/22 |
| 6,294,136 B1 | * | 9/2001 | Schwartz ..................... 422/186 |
| 6,625,585 B1 | | 9/2003 | MacCuish et al. |

FOREIGN PATENT DOCUMENTS

WO    WO 98/47087    10/1998

OTHER PUBLICATIONS

Hibert et al. "Graphics Computer–Aided Receptor Mapping as a Predicitve Tool for Drug Design: Development of Potent, Selective, and Stereospecific Ligans for the 5–HT1A Receptor." J. Med. Chem., 1988, vol 31, pp. 1087–1093, Supplementary Mat. pp. 32–34.* van Osdol, W. W. et al., "Use of the Kohonen Self–organizing Map to Study the Mechanisms of Action of Chemotherpeutic Agents", *Journal of the National Cancer Institute*, 86:1853–1859 (1994).

Ornstein, L., "Computer Learning and the Scientific Method: A Proposed Solution to the Information Theoretical Problem of Meaning", *Journal of the Mount Sinai Hospital*, XXXII:437–494 (1965).

(Continued)

*Primary Examiner*—Wilbert L. Starks, Jr.

(57) ABSTRACT

A system for analyzing a vast amount of data representative of chemical structure and activity information and concisely providing conclusions about structure-to-activity relationships. A computer may adaptively learn new substructure descriptors based on its analysis of the input data. The computer may then apply each substructure descriptor as a filter to establish new groups of molecules that match the descriptor. From each new group of molecules, the computer may in turn generate one or more additional new groups of molecules. A result of the analysis in an exemplary arrangement is a tree structure that reflects pharmacophoric information and efficiently establishes through lineage what effect on activity various chemical substructures are likely to have. The tree structure can then be applied as a multi-domain classifier, to help a chemist classify test compounds into structural subclasses.

72 Claims, 13 Drawing Sheets

OTHER PUBLICATIONS

Barnard, J. M. and Downs, G. M., "Clustering of Chemical Structures on the Basis of Two–Dimensional Similarity Measures", *Journal of Chemical Information and Computer Sciences*, 32:644–649 (1992).

Grethe, G. and Hounshell, W. D., "Similarity Searching in the Development of New Bioactive Compounds. An Application." *Chemical Structure Proceedings International Conference*, pp. 399–407 (1993).

King, R. D. et al., "Comparison of Artificial Intelligence Methods for Modeling Pharmaceutical Qsars", *Applied Artificial Intelligence*, 9:213–233 (1995).

Jain, K. J. et al., "Algorithms for Clustering Data", *Algorithms for Clustering Data*, pp. 96–101 (1988).

Downs, G. M. and Willett, P., Similarity Searching and Clustering of Chemical–Structure Databases Using Molecular Property Data, *J. Chem. Inf. Comput. Sci.* 34: 1094–1102 (1994).

Kearsley, S. K. et al., Chemical Similarity Using Physicochemical Property Descriptors, *J. Chem. Inf. Comput. Sci.* 36: 118–127 (1996).

Brown, R. D. et al., Matching Two–Dimensional Chemical Graphs Using Genetic Algorithms, *J. Chem. Inf. Comput. Sci.* 34: 63–70 (1994).

Brown, R. D. and Martin, Y.C., Use of Structures—Activity of Data to Compare Structure–Based Clustering Methods and Descriptors for Use in Compound Selection, *J. Chem. Inf. Comput. Sci.* 36:572–584 (1996).

Discriminant Analysis and Clustering—Panel on Discriminant Analysis, Classification and Clustering. *Statistical Science* 4: 34–69 (1989).

Regalado, A., Preclinical Strategies—Drug Development's Preclinical Bottleneck, *Start–Up* pp. 26–37 (Dec. 1997).

Longman, R., Marketplace Strategies—Screening the Screeners, *Start–Up* pp. 14–22 (Sep. 1997).

Thayer, A. M., Combinatorial chemistry becoming core technology at drug discovery companies, *C & EN* pp. 57–64 (Feb. 1996).

Combinatorial Chemistry—Combinatorial chemists focus on small molecules, molecular recognition, and automation, *C & EN* pp. 28–54 (Feb. 1996).

Kohonen, Self–Organizing Maps, Springer pp. 85–144. (1995).

Chen, X. et al., Recursive Partitioning Analysis of a Large Structure–Activity Data Set Using Three–Dimensional Descriptors[1], *J. Chem. Inf. Comput. Sci.* (1998).

James, C. A. et al., Daylight Theory Manual Daylight 4.61, Daylight Chemical Information Systems, Inc., Version 11 Feb., 1997.

Weininger, D., SMILES, a Chemical Language and Information System. 1. Introduction to Methodology and Encoding Rules. *J. Chem. Inf. Comput. Sci.* 28: 31–36 (1988).

Cook, D.J. et al., Knowledge Discovery from Stuctural Data. *Journal of Intelligence and Information Sciences*, vol. 5, No, 3, pp. 229–245 (1995).

Djoko, S. et al., An Empirical Study of Domain Knowledge and its Benefits to Substructure Discovery. In *IEEE Transactions on Knowledge and Data Engineering*, vol. 9, No. 4, pp. 1–13 (1997).

Galal, G. et al., Improving Scalability in a Knowledge Discovery System by Exploiting Parallelism. In the Proceedings of the Third International Conference on Knowledge Discovery and Data Mining, pp. 171–174 (1997).

Holder, L. B. and D. J. Cook. Discovery of Inexact Concepts from Structural Data. In *IEEE Transactions of Knowledge and Data Engineering*, vol. 5,No. 6, pp. 992–994 (1993).

Holder, L. B. et al., Fuzzy Substructure Discovery. In *Proceedings of the Ninth International Conference on Machine Learning*, pp. 218–223 (1992).

Cook, D. J. et al., Scalable Discovery of Informative Structural Concepts Using Domain Knowledge. In *IEEE Expert*, vol. 11, No. 5, pp. 59–68 (1996).

Aude, J.C. et al., Applications of the pyramidal clustering method to biological objects. Computers & Chemistry 23: 301–315 (1999).

Bertrand, P., Structural Properties of Pyramidal Clustering. DIMACS Series in Discrete Mathematics and Theoretical Computer Science, 19: 35–53 (1995).

Fausett, L., Fundamentals of Neural Networks: Architectures, Algorithms, and Applications. pp. 169–188 (1994).

Godden, Jeffrey W., et al. Combinatorial Preferences Affect Molecular Similarity/Diversity Calculations Using Binary Fingerprints and Tanimoto Coefficients. *J. Chem. Inf. Comput. Sci.* 2000, vol. 40, pp. 163–166.

Downs, G.M. and Willett, P., "Similarity Searching and Clustering of Chemical–Structure Databases Using Molecular Property Data", *J. Chem. Inf. Comput. Sci.* 34:1094–1102 (1994).

Kearsley, S.K. et al., Chemical Similarity Using Physicochemical Property Descriptors, *J. Chem. Inf. Comput. Sci*, 36:118–127 (1996).

Brown, R.D., et al., Matching Two–Dimensional Chemical Graphs Using Genetic Algorithms, *J. Chem. Inf. Comput. Sci.* 34:63–70 (1994).

Brown, R.D. and Martin, Y.C., Use of Structure–Activity Data to Compare Structure–Based Clustering Methods and Descriptors for Use in Compound Selection, *J. Chem. Inf. Comput. Sci.* 36:572–584 (1996).

Barnard, J.M. and Downs, G.M., Chemical Fragment Generation and Clusteriing Software, Product Descriptions, Jun. 27, 1996.

Kohonen, T., Self–Organizing Maps, Springer, pp. 85–144.

Longman, R., Marketplace Strategies—Screening the Screeners. *Start–Up*, pp. 14–22 (Sep. 1997).

Thayer, A.M., Combinatorial Chemistry becoming core technology at drug discovery companies. *C & EN*, pp. 57–67 (Feb. 1996).

Goodacre, R. et al., Quantitative Alanysis of Multivariate Data using Artificial Neural Networks: A Tutorial Review and Applications to the Deconvolution of Pyrolysis Mass Spectra, *Tutorial from >I≦ Zentralblatr fur Bakteriologie* (1999).

James, C.A. et al., Daylight Theory Manual Daylight 4.61, Daylight Chemical Information Systems, Inc., Version 11 (Feb. 1997).

Labute, P., Binary QSAR: A new Technology for HTS and UHTS Data Analysis, Chemical Computing Group, Inc. In *Journal of the Chemical Computing Group* (1998).

From the World Wide Web: www.netsci.org, Network Science—Welcome to NetSci's Lists of Computational Chemistry Software (1999), printed Feb. 8, 1999.

From the World Wide Web: www.netsci.org: Network Science—Welcome to NetSci's Combinatorial Chemistry and Mass Screening YellowPages (1999), printed Feb. 8, 1999.

Weininger, D., SMILES, a Chemical Language and Information System, 1. Introduction to Methodology and Encoding Rules. *J. Chem. Inf. Comput. Sci.*, 28: 31–36 (1988).

Holder, L. B. et al., Fuzzy Substructure Discovery. In *Proceedings of the Ninth International Conference on Machine Learning*, pp. 218–223 (1992).

Djoko, S. et al., Analyzing the Benefits of Domain Knowledge in Substructure Discovery. In *Proceedings of the First International Conference on Knowledge Discovery and Data Mining*, pp. 75–80 (1995).

Aude, J.C. et al., Application of the pyramidal clustering method to biological objects. Computers & Chemistry 23: 301–315 (1999).

"Pyramids" Homepage: Including http://bioweb.pasteur.fr/docs-gensoft/pyramids/QuickStart.

From the World Wide Web: http://www.tripos.com/software/charisma.html, printed Feb. 15, 2000.

From the World Wide Web: http://www.tripos.com/about/press/1999/1999.03.23.html, printed Feb. 15, 2000.

Hibert et al., "Graphics Computer–Aided Receptor Mapping as a Predictive Tool for Drug Design: Development of potent Selective, and Stereospecific Ligands for the 5–HT1A Receptor," *J. Med Chem*, 31:1087–1093, 1988.

Office Action from Application No. 09/549,746, dated Jul. 30, 2002.

Office Action from Application No. 09/281,990, dated Jun. 4, 2002.

Office Action from Application No. 09/281,990, dated Jul. 16, 2001.

U.S. patent application Ser. No. 10/649,596, filed Aug. 27, 2003 entitled "Method and System for Artificial Intelligence Directed Lead Discovery in High Throughput Screening Data".

* cited by examiner

Figure 3a

| Exemplary Starting Keys ||||
|---|---|---|---|
| SMARTS Query | Minimum hits | Weight | Comment and corresponding MACCS definition, if any |
| [R2;r5]~[R2;r5] | 1 | 7 | 1 Any double ring, structure with the smallest ring a 5 member ring |
| [R2;r6]~[R2;r6] | 1 | 7 | 2 Any double ring structure with the smallest ring a 6 member ring |
| [!#6;r4][r4][r4][r4] | 1 | 100 | 3 QAAA@1 |
| [#4,#12,#20,#38,#56,#88] | 1 | 100 | 4 Group IIA |
| [r4] | 1 | 100 | 5 4 M ring |
| [#29,#30,#47,#48,#79,#80] | 1 | 95 | 6 group IB,IIB |
| [#8]~[#7](~[#6])~[#6] | 1 | 100 | 7 ON(C)C |
| [#16]-[#16] | 1 | 100 | 8 S-S |
| [#8]~[#6](~[#8])~[#8] | 1 | 100 | 9 OC(O)O |
| [!#6]1~*~*1 | 1 | 100 | 10 QAA@1 |
| C#C | 1 | 85 | 11 CTC |
| [#5,#13,#31,#49,#81] | 1 | 76 | 12 Group IIIA |
| [r7] | 1 | 90 | 13 7 M ring |
| [#14] | 1 | 40 | 14 Si |
| [#6]=[#6](~[!#6])~[!#6] | 1 | 56 | 15 C=C(Q)Q |
| [r3] | 1 | 80 | 16 3 M ring |
| [#7]~[#6](~[#8])~[#8] | 1 | 18 | 17 NC(O)O |
| [#7]-[#8] | 1 | 9 | 18 N-O |
| [#7]~[#6](~[#7])~[#7] | 1 | 45 | 19 NC(N)N |
| [#6;R]=[#6;R](@*)@* | 1 | 35 | 20 C$=C($A)($A) |
| [#53] | 1 | 40 | 21 I |
| [!#6][CH2][!#6] | 1 | 57 | 22 QCH2Q |
| [#15] | 1 | 20 | 23 P |
| [#6]~[!#6](~[#6])(~[#6])~* | 1 | 29 | 24 CQ(C)(C)A |
| [!#6]~[#9,#17,#35,#53] | 1 | 23 | 25 QX |
| [#6]~[#16]~[#7] | 1 | 50 | 26 CSN |
| [#7]~[#16] | 1 | 46 | 27 NS |
| [CH2]=,:* | 1 | 26 | 28 CH2=A |
| [#16;r] | 1 | 30 | 29 S heterocycle |
| [#7]~[#6](~[#8])~[#7] | 1 | 12 | 30 NC(O)N |
| [#7]~[#6](~[#6])~[#7] | 1 | 20 | 31 NC(C)N |
| [#8]~[#16](~[#8])~[#8] | 1 | 25 | 32 OS(O)O |
| [#16]-[#8] | 1 | 25 | 33 S-O |
| C#N | 1 | 24 | 34 CTN |
| [#9] | 1 | 12 | 35 F |
| [!#6;H1,H2,H3]~*~[!#6;H1,H2,H3] | 1 | 10 | 36 QHAQH |
| [#6]=[#6]~[#7] | 1 | 14 | 37 C=CN |
| [#35] | 1 | 14 | 38 Br |
| [#16]~*~[#7] | 1 | 15 | 39 SAN |

Figure 3b

| Exemplary Starting Keys Cont. | | | |
|---|---|---|---|
| SMARTS Query | Minimum hits | Weight | Comment and corresponding MACCS definition, if any |
| [#8]~[!#6](~[#8])~[#8] | 1 | 10 | 40 OQ(O)O |
| [-,--,---,+,++,+++] | 1 | 6 | 41 charge |
| [#6]=[#6](~[#6])~[#6] | 1 | 11 | 42 C=C(C)C |
| [#6]~[#16]~[#8] | 1 | 14 | 43 CSO |
| [#7]~[#7] | 1 | 12 | 44 NN |
| [!#6;H1,H2,H3]~*~*~*[!#6;H1,H2,H3] | 1 | 10 | 45 QHAAAQH |
| [!#6;H1,H2,H3]~*~*[!#6;H1,H2,H3] | 1 | 8 | 46 QHAAQH |
| [#8]~[#16]~[#8] | 1 | 13 | 47 OSO |
| [#8]~[#7](~[#8])~[#6] | 1 | 11 | 48 ON(O)C |
| [#8;r] | 1 | 8 | 49 O heterocycle |
| [!#6]~[#16]~[!#6] | 1 | 12 | 50 QSQ |
| [#16]!:*:* | 1 | 12 | 51 Snot%A%A |
| [#16]=,:[#8] | 1 | 13 | 52 S=O |
| *~[#16](~*)~* | 1 | 12 | 53 AS(A)A |
| *@*!@*@* | 1 | 11 | 54 A$A!A$A |
| [#7]=,:[#8] | 1 | 11 | 55 N=O |
| *@*!@[#16] | 1 | 11 | 56 A$A!S |
| [#6]:[#7] | 1 | 12 | 57 C%N |
| [#6][#6](([#6])([#6]))* | 1 | 9 | 58 CC(C)(C)A |
| [!#6]~[#16] | 1 | 11 | 59 QS |
| [!#6;H1,H2,H3]~[!#6;H1,H2,H3] | 1 | 8 | 60 QHQH(&..) |
| [!#6]~[!#6;H1,H2,H3] | 1 | 8 | 61 QQH |
| [!#6]~[#7]~[!#6] | 1 | 9 | 62 QNQ |
| [#7]~[#8] | 1 | 9 | 63 NO |
| [#8]~*~*~[#8] | 1 | 7 | 64 OAAO |
| [#16]=,:* | 1 | 8 | 65 S=A |
| [#6H3]~*~[#6H3] | 1 | 6 | 66 CH3ACH3 |
| *!@[#7]@* | 1 | 8 | 67 A!N$A |
| [#6]=[#6](~*)~* | 1 | 6 | 68 C=C(A)A |
| [#7]~*~[#7] | 1 | 5 | 69 NAN |
| [#6]=[#7] | 1 | 6 | 70 C=N |
| [#7]~*~*~[#7] | 1 | 6 | 71 NAAN |
| [#7]~*~*~*~[#7] | 1 | 6 | 72 NAAAN |
| [#16]~*(~*)~* | 1 | 7 | 73 SA(A)A |
| *~[#6H2]~[!#6;H1,H2,H3,H4] | 1 | 6 | 74 ACH2QH |
| [!#6;!#1;r5]1~[r5]~[r5]~[r5]~[r5]1 | 1 | 5 | 75 QAAAA@1 |
| [#7;H2,H3,H4] | 1 | 6 | 76 NH2 |
| [#6]~[#7](~[#6])~[#6] | 1 | 5 | 77 CN(C)C |
| [#6;H2,H3]~[!#6]~[#6;H2,H3] | 1 | 5 | 78 CH2QCH2 |
| [#9,#17,#35,#53]!@*@* | 1 | 4 | 79 X!A$A |

Figure 3c

| Exemplary Starting Keys Cont. | | | |
|---|---|---|---|
| SMARTS Query | Minimum hits | Weight | Comment and corresponding MACCS definition, if any |
| [#16] | 1 | 5 | 80 S |
| [#8]~*~*~*~[#8] | 1 | 4 | 81 OAAAO |
| [!#6;H1,H2,H3]~*~*~[#6;H2]~* | 1 | 4 | 82 QHAACH2A |
| [!#6;H1,H2,H3]~*~*~*[#6;H2]* | 1 | 4 | 83 QHAAACH2A |
| [#8]~[#6](~[#7])~[#6] | 1 | 4 | 84 OC(N)C |
| [!#6;!#1]~[CH3] | 1 | 4 | 85 QCH3 |
| [!#6;!#1]~[#7] | 1 | 4 | 86 QN |
| [#7]~*~*~[#8] | 1 | 4 | 87 NAAO |
| [r5] | 1 | 4 | 88 5M ring |
| [#7]~*~*~*~[#8] | 1 | 5 | 89 NAAAO |
| [!#6]1~*~*~*~*~*1 | 1 | 5 | 90 QAAAAA@1 |
| [#6]=[#6] | 1 | 4 | 91 C=C (does not hit aromatic) |
| *~[#6H2]~[#7] | 1 | 4 | 92 ACH2N |
| [r8,r9,r10,r11,r12,r13,r14] | 1 | 4 | 93 8M ring or larger |
| [!#6]~[#8] | 1 | 3 | 94 QO |
| [#17] | 1 | 4 | 95 CL |
| [!#6;H1,H2,H3]~*~[CH2]~* | 1 | 4 | 96 QHACH2A |
| *@*(@*)@* | 1 | 4 | 97 A$A($A)$A |
| [!#6;!#1]~*(~[!#6;!#1])~[!#6;!#1] | 1 | 2 | 98 QA(Q)Q |
| [#9,#17,#35,#53]~*(~*)~* | 1 | 3 | 99 XA(A)A |
| [CH3]~*~*~[CH2]~[!#1] | 1 | 4 | 100 CH3AAACH2A |
| *~[#6;H3,H2]~[#8] | 1 | 4 | 101 ACH2O |
| [#7]~[#6]~[#8] | 1 | 3 | 102 NCO |
| [#7]~*~[#6;H2]~* | 1 | 4 | 103 NACH2A |
| *~*(~*)(~*)~* | 1 | 3 | 104 AA(A)(A)A |
| [#8]!:*:* | 1 | 4 | 105 Onot%A%A |
| [CH3]~[#6;H2]~* | 1 | 3 | 106 CH3CH2A |
| [CH3]~*~[#6;H2]~* | 1 | 3 | 107 CH3ACH2A |
| [CH3]~*~*~[#6;H2]~* | 1 | 3 | 108 CH3AACH2A |
| [#7]~*~[#8] | 1 | 2 | 109 NAO |
| *~[CH2][CH2]~* | 3 | 3 | 110 ACH2CH2A > 1 |
| [#7]=,:* | 1 | 3 | 111 N=A |
| [!#6&r] | 2 | 3 | 112 heterocycle atom > 1 & other features |
| [#7&r] | 1 | 4 | 113 N heterocycle |
| *~[#7](~*)~* | 1 | 3 | 114 AN(A)A |
| [#8]~[#6]~[#8] | 1 | 3 | 115 OCO |
| [!#6]~[!#6] | 1 | 2 | 116 QQ |
| a | 7 | 2 | 117 aromatic ring > 1 |
| *!@[#8]!@* | 1 | 2 | 118 A!O!A |

Figure 3d

| Exemplary Starting Keys Cont. | | | |
|---|---|---|---|
| SMARTS Query | Minimum hits | Weight | Comment and corresponding MACCS definition, if any |
| *@*!@[#8] | 2 | 2 | 119 A$A!O > 1 & ... |
| *[CH2]*~*~*[CH2]* | 1 | 3 | 120 ACH2AAACH2A |
| *~[#6&H2]~*~*~[#6&H2]~* | 1 | 3 | 121 ACH2AACH2A |
| [!#6]~[!#6] | 2 | 2 | 122 QQ > 1 |
| [!#6;H1,H2,H3,H4] | 2 | 2 | 123 QH > 1 |
| [#8]~*[CH2]* | 1 | 2 | 124 OACH2A |
| *@*!@[#7] | 1 | 2 | 125 A$A!N |
| [#9,#17,#35,#53] | 1 | 2 | 126 X (halogen) |
| [#7]!:*:* | 1 | 2 | 127 Nnot%A%A |
| [#8]=,:* | 2 | 2 | 128 O=A>1 |
| [!#6&r] | 1 | 3 | 129 heterocycle |
| [!#6]~[CH2]~* | 2 | 2 | 130 QCH2A>1 & ... |
| [#8;H1,H2] | 1 | 2 | 131 OH |
| [#8] | 4 | 2 | 132 O > 3 and other features .. |
| [CH3] | 3 | 2 | 133 CH3 > 2 |
| [#7] | 2 | 2 | 134 N>1 |
| *@*!@[#8] | 1 | 2 | 135 A$A!O |
| *!:*:*!:* | 1 | 2 | 136 Anot%A%Anot%A |
| [r6] | 7 | 2 | 137 6 M ring > 1 |
| [#8] | 3 | 2 | 138 O > 2 |
| *~[CH2]~[CH2]~* | 1 | 2 | 139 ACH2CH2A |
| *~[!#6](~*)~* | 1 | 2 | 140 AQ(A)A |
| [CH3] | 2 | 2 | 141 CH3 > 1 |
| *!@*@*!@* | 1 | 2 | 142 A!A$A!A |
| [#7;H1,H2,H3,H4] | 1 | 2 | 143 NH |
| [#8]~[#6](~[#6])~[#6] | 1 | 2 | 144 OC(C)C |
| [!#6][CH2]* | 1 | 2 | 145 QCH2A |
| [#6]=,:O | 1 | 1 | 146 C=O |
| *!@[CH2]!@* | 1 | 1 | 147 A!CH2!A |
| [#7]~*(~*)~* | 1 | 1 | 148 NA(A)A |
| [#6]-[#8] | 1 | 1 | 149 C-O |
| [#6]-,:[#7] | 1 | 1 | 150 C-N |
| [#8] | 2 | 1 | 151 O > 1 |
| [CH3] | 1 | 1 | 152 CH3 |
| [#7] | 1 | 1 | 153 N |
| a | 1 | 1 | 154 aromatic |
| [r6] | 1 | 1 | 155 6 member ring |
| [#8] | 1 | 1 | 156 O |
| R | 1 | 1 | 157 ring |

METHOD AND SYSTEM FOR ARTIFICIAL INTELLIGENCE DIRECTED LEAD DISCOVERY THROUGH MULTI-DOMAIN CLUSTERING

RELATED APPLICATIONS

This application claims priority to U.S. provisional patent application No. 60/120,701, entitled "Artificial Intelligence Directed Lead Discovery," filed Feb. 19, 1999, by Susan 1. Bassett, Andrew P. Dalke, John W. Elling, Brian P. Kelley, Christodoulos A. Nicolaou, and Ruth F. Nutt, the entirety of which is hereby incorporated herein by reference.

This application also claims priority to U.S. patent application Ser. No. 09/281,990, entitled "Method and System for Artificial Intelligence Directed Lead Discovery in High Throughput Screening Data," filed Mar. 29, 1999, by John W. Elling and Susan I. Bassett, the entirety of which is hereby incorporated herein by reference.

This application is also related to a U.S. provisional patent application filed on Feb. 18, 2000, by John D. MacCuish and Christodoulos A. Nicolaou, entitled "Method and System for Artificial Intelligence Directed Lead Discovery Through Multi-Domain Agglomerative Clustering," which is owned by the owner of the present invention, and the entirety of which is hereby incorporated herein by reference.

COPYRIGHT

A portion of this disclosure of this patent document contains material that is subject to copyright protection. The copyright owner has no objection to the facsimile reproduction by anyone of the patent disclosure, as it appears in the Patent and Trademark Office patent files or records, but otherwise reserves all United States and International copyright rights whatsoever.

BACKGROUND OF THE INVENTION

1. Field of the Invention

The present invention relates to computer-based analysis of data and generally to the computer-based correlation of data features with data responses, in order to determine or predict which features correlate with or are likely to result in one or more responses. The invention is particularly suitable for use in the fields of chemistry, biology and genetics, such as to facilitate computer-based correlation of chemical structures with observed or predicted pharmacophoric activity. The invention is particularly useful in facilitating the identification and development of potentially beneficial new drugs.

For purposes of illustration, the invention will be described primarily in the context of computer-based analysis of chemical structure-activity relationships (SAR). However, based on the present disclosure, those of ordinary skill in the art will appreciate that the invention may be applicable in other areas as well. By way of example and without limitation, the invention may be applicable in genetics and antibody-protein analysis.

2. Description of Related Art

The global biotech and pharmaceutical industry is a $200 billion/year business. Most of the estimated $13 billion R&D spending in this industry is focused on discovering and developing prescription drugs. Current R&D effort is characterized by low drug discovery rates and long time-to-market.

In an effort to accelerate drug discovery, biotech and pharmaceutical firms are turning to robotics and automation. The old methods of rationally designing molecules using known structural relationships are being supplanted by a shotgun approach of rapidly screening hundreds of thousands of molecules for biological activity. High Throughput Screening (HTS) is being used to test large numbers of molecules for biological activity. The primary goal is to identify hits or leads, which are molecules that affect a particular biological target in the desired manner. For instance and without limitation, a lead may be a chemical structure that binds particularly well to a protein.

Automated HTS systems are large, highly automated liquid handling and detection systems that allow thousands of molecules to be screened for biological activity against a test assay. Several pharmaceutical and biotech companies have developed systems that can perform hundreds of thousands of screens per day.

The increasing use of HTS is being driven by a number of other developments in the industry. The greater the number and diversity of molecules that are run through screens, the more successful HTS is likely to be. This fact has propelled rapid developments in molecule library collection and creation. Combinatorial chemistry systems have been developed that can automatically create hundreds of thousands of new molecules. Combinatorial chemistry is performed in large automated systems that are capable of synthesizing a wide variety of small organic molecules using combinations of "building block" reagents. HTS systems are the only way that the enormous volume of new molecules generated by combinatorial chemistry systems can be tested for biological activity. Another force driving the increased use of HTS is the Human Genome program and the companion field of bioinformatics that is enabling the rapid identification of gene function and accelerating the discovery of therapeutic targets. Companies do not have the resources to develop an exhaustive understanding of each potential therapeutic target. Rather, pharmaceutical and biotech companies use HTS to quickly find molecules that affect the target and may lead to the discovery of a new drug.

High throughput screening does not directly identify a drug. Rather the primary role of HTS is to detect lead molecules and supply directions for their optimization. This limitation exists because many properties critical to the development of a successful drug cannot be assessed by HTS. For example, HTS cannot evaluate the bioavailability, pharmacokinetics, toxicity, or specificity of an active molecule. Thus, further studies of the molecules identified by HTS are required in order to identify a potential lead to a new drug.

The further study, a process called lead discovery, is a time- and resource-intensive task. High throughput screening of a large library of molecules typically identifies thousands of molecules with biological activity that must be evaluated by a pharmaceutical chemist. Those molecules that are selected as candidates for use as a drug are studied to build an understanding of the mechanism by which they interact with the assay. Scientists try to determine which molecular properties correlate with high activity of the molecules in the screening assay. Using the drug leads and this mechanism information, chemists then try to identify, synthesize and test molecules analogous to the leads that have enhanced drug-like effect and/or reduced undesirable characteristics in a process called lead optimization. Ideally, the end result of the screening, lead discovery, and lead optimization is the development of a new drug for clinical testing.

As the number of molecules in the test library and the number of therapeutic target assays exponentially increase, lead discovery and lead optimization have become the new bottleneck in drug discovery using HTS systems. Because of the large number of HTS results that must be analyzed, scientists often seek only first-order results such as the identification of molecules in the library that exhibit high assay activity. In one method, for instance, all of the molecules in the data set are divided into groups based on common properties of their molecular structures. An analysis is then made to determine which groups contain molecules with high activity levels and which groups contain molecules with low activity levels. Those groups representing high activity levels are then deemed to be useful groups. Commonly, the analysis will stop at this point, leaving chemists to analyze the members of the active groups in search of new or optimized leads.

In another method, for instance, a more extensive automated analysis is conducted in an effort to partition the molecules into groups of particular interest and particularly to derive structure-activity relationship rules. An example of this method is described in International Patent Application No. PCT/US98/07899 (designating the United States), filed Apr. 17, 1998 by Glaxo Group Ltd., published as International Publication No. WO 98/47087 on Oct. 22, 1998, and further by Xin Chen et al., "Recursive Partitioning Analysis of a Large Structure-Activity Data Set Using Three-Dimensional Descriptors" (University of North Carolina, and Glaxo Welcome, Inc., May 17, 1998), both of which are expressly incorporated herein by reference in their entireties.

As described by Glaxo and Chin et al., well known recursive partitioning (RP) techniques, commonly referred to as classification trees, are used to iteratively partition a data set (such as results of HTS or other automated chemical synthesis) into active classes. The data set includes molecules and indicia of empirically determined potency (activity-level) per molecule. According to the method, a set of descriptors is first provided, each indicating structural feature that can be described as present or absent in a given molecule. For each molecule, a bit string is then built, indicating whether the molecule has each particular descriptor (1-bit) or not (0-bit). These strings are then configured as a matrix, in which each row represents a molecule and each column represents a descriptor. RP is then used to divide the molecules (rows) into exactly two groups according to whether the molecules have a particular "best" descriptor in common. The "best" descriptor is the descriptor that would result in the largest possible difference in average potency between those molecules containing the descriptor and those molecules not containing the descriptor.

As further described, the method continues iteratively with respect to each subdivided group, dividing each group into two groups based on a next "best" descriptor selected from the group of descriptors. The result of this process is a tree structure, in which some terminal nodes may contain a preponderance of inactive molecules (or molecules having relatively low potency) and other terminal nodes may contain a preponderance of active molecules (or molecules having relatively high potency) (the latter being "good terminal nodes"). Tracing the lineage of the structures defined by a good terminal node may then reveal molecular components that cooperatively reflect a high likelihood of potency. After generating the tree structure through use of RP, it is possible to predict the activities of molecules that have not yet been empirically tested for activities. In particular, a known molecule can be passed down through the tree and examined for the presence or absence of descriptors established to confer activity. HTS or other analysis can then be efficiently conducted with respect to only those molecules that have at least a threshold level of predicted activity.

The present inventors have discovered that the use of RP to partition molecules on the basis of their structural and activity similarity is limiting. By way of example, with RP, each molecule can fall within only a single terminal node of the tree structure, based on one or more determinations along the way as to whether the molecule includes various descriptors known to confer activity. Consequently, if there may be more than one set of descriptors in a molecule (or set of molecules) that results in observed activity, RP may be unable to identify all of the pertinent descriptor sets.

For instance, given an initial set of 10 molecules, assume that the molecules are first partitioned on the basis of descriptor A into groups A0 and A1, where group A0 contains 3 low-potency molecules not having A and group A1 contains 7 high-potency molecules having A. Assume that the 7 high-potency molecules are then partitioned on the basis of descriptor B into groups B0 and B1, where group B0 contains 2 low-potency molecules not having B and group B1 contains 5 high-potency molecules having B. Finally, assume that the 5 high-potency molecules are then partitioned on the basis of descriptor C into groups C0 and C1, where group C0 contains 3 low potency molecules not having C. As a result, a reasonable conclusion is that molecules having descriptors A, B and C are likely to have a high degree of potency. However, assume further that there exists another descriptor D, and that if the original group of 10 molecules were divided on the basis of descriptor D, the tree would grow a different set of branches, indicative of a different set of descriptors corresponding to a high degree of potency. Unfortunately, since the RP method necessarily partitions molecules into mutually exclusive groups, it is unable to discover that lead candidates might in fact be optimized along two or more different pathways or branches.

A thorough exploration of numerous RP trees generated with the same data set, using a collection of methods, such as selective elimination of some features, or changing the splitting criterion, or performing surrogate splits, can create alternative sets of descriptors for the same molecule or set of molecules. However, these procedures would require a great deal of time and effort on the part of the user. It is often very difficult to find a consensus among the vast number of possible reasonable trees that can be useful in building a predictive model.

In addition, if the size of the two classes is significantly unbalanced as is often the case with active and inactive classes in a large diverse population of compounds (where typically 5% or less show as active in a high-throughput screen), building a classifier and hence a predictive model can be considerably more difficult. A small amount of noise in the data will often prevent the descriptors from discriminating the very small class from the much larger class. Unfortunately, in HTS, particularly in early screening, the noise level of the response is notoriously high, and the levels of false positive and false negative responses for molecules can be high. The present inventors have discovered that this noise level may contribute to compromised or faulty splitting decisions for the RP tree.

SUMMARY OF THE INVENTION

The present invention provides a computer-based system (such as a method, apparatus (e.g., disk or other storage medium bearing a machine-executable instructions) and/or machine) for identifying and correlating relationships between features and responses in a data set. In the chemistry field, for instance, the invention provides a computer-based system for generating structure-to-activity relationship (SAR) information and pharmacophore models for each pharmacophoric mechanism identified in the HTS screen of a diverse (heterogeneous) library. In this context, the term "mechanism" means the different ways for the molecules in the library to interact with a specified target. A mechanism model or pharmacophore can be a multi-dimensional arrangement of physical and structural features that enable a molecule to interact with a target through a specific interaction with the target's active site.

As noted above, existing analysis systems typically involve (i) dividing a set of molecules into subclasses based on structural similarity and then identifying which subclass represents higher potency and is therefore of interest for further study, or (ii) dividing a set of molecules into subclasses based on differences in potency for given structural features. The existing art thus addresses the question of how well a given subclassification distinguishes active molecules from inactive molecules.

According to one aspect, an exemplary embodiment of the present invention includes a system for adaptively learning what substructure(s) are responsible for subclassifications of chemical molecules, even where those subclassifications divide active molecules from other active molecules (rather than strictly active from inactive). In an exemplary embodiment, the adaptive learning system may operate for instance by grouping a set of molecules according to their molecular structure as characterized by a set of descriptors, identifying the groups that represent a high level of activity, and analyzing those groups to identify the most common substructure(s) among the molecules in the groups, which may reasonably be correlated to the observed activity level. Thus, rather than merely determining how well a particular subgroup distinguishes active molecules from inactive molecules, the present invention may go further and determine the reason or reasons for the distinction: namely, the responsible substructures.

According to a further aspect, these adaptively learned substructures may then serve as a basis for further classifying the molecules in order to identify pharmacophoric mechanisms or processes (e.g., rules) for building pharmacophores. In particular, in an exemplary embodiment, each adaptively learned substructure may be used as a filter through which the molecules may be passed. For each filter, a new "child" node based on the filter may then comprise those molecules that include the corresponding substructure.

By iteratively continuing this process of identifying substructures and using the substructures as filters to further group the molecules, the invention advantageously establishes a multi-domain tree structure. In the exemplary embodiment, each node of the tree structure (after the root node) defines a pharmacophoric mechanism (e.g., substructure) that is adaptively learned from its parent node, and node represents or comprises one or more molecules that include that mechanism. From each node, one or more children nodes is then created, each preferably defining a further pharmacophoric mechanism, and each including those molecule(s) from its parent node that include the mechanism. According to the exemplary embodiment, branches of the tree structure can be pruned (i.e., not further developed) once a determination is made that no new information of sufficient interest can be gleaned.

Consequently, an exemplary embodiment provides a system for simultaneously classifying individual molecules into multiple structural subclasses, rather than necessarily partitioning the group of molecules into mutually exclusive groups. The system thus provides improved means for developing multiple structural classes related to activity, and building improved tree structures that embody information about development of pharmacophoric mechanisms. From any given node of the tree, if a molecule includes more than one of the substructures adaptively learned from the node, the molecule can fall into a plurality of children nodes. Consequently, the information that is defined by that molecule (e.g., its structure and activity) is not then restricted to use in building a single branch of the tree, but, rather, can be usefully considered in building multiple branches at once.

The end result of this process is more information, and more useful information at that. In fact, a tree structure produced in accordance with an exemplary embodiment of the invention can represent, in and of itself, a tremendous amount of commercially valuable information, much of which was previously unavailable to those of ordinary skill in the art. As an example, for each node of the tree (after the root node), the pharmacophoric mechanism that defines the filter used to establish the node can be commercially valuable information, since it represents a substructure that is likely to be responsible for observed pharmacophoric activity. Such a substructure might therefore be usefully employed to develop beneficial new drugs.

In turn, any lineage of nodes in the tree (e.g., from a given node up or down to another node) can embody a significant amount of commercially valuable information. By the time one or more molecules reaches a terminal node ("leaf") of the tree, for instance, each such molecule may have passed through a number of filters defining its ancestral parent node(s). This ancestral line of filters may therefore represent the pharmacophoric mechanisms that, cooperatively, are likely to result in an activity level reflected by the molecule(s) in the terminal node.

As another example, each split in the tree that gives rise to a plurality of children nodes represents a plurality of different ways that a given chemical substructure (represented by the parent node in the split) can be modified to achieve different pharmacophoric mechanisms. The information provided by such splits is particularly valuable where the split results in a plurality of children nodes that contain overlapping sets of molecules (e.g., where one or more molecules of the parent node satisfies the filter of a plurality of children nodes), since, with such a result, each child node branch is more likely represent a separate scientifically interesting pharmacophoric mechanism.

As yet another example, the difference in activity levels between molecules in a child node and molecules in its parent node can be very valuable information, since the difference may represent the enhancing or detracting effect of the pharmacophoric mechanism that gave rise to the child node. Such information is even more valuable when a given parent node gives rise to multiple children nodes and the activity differential varies greatly among the children nodes. For instance, if one child node reflects an activity increase compared to the parent, while the other children nodes reflect activity decreases compared to the parent, it is reasonable to conclude that the pharmacophoric mechanism defined by the one child node is likely to be more useful for development of beneficial new drugs.

According to yet a further aspect, an exemplary embodiment of the invention preferably provides as output a description (or indication) of all or part of the resulting tree. This output may, for instance, describe the various nodes and branches comprising the tree, either graphically, in text, or in any other desired form. For each node of the tree, the output may indicate the adaptively learned substructure (e.g., pharmacophoric mechanism) that gave rise to the node. In addition, the output may indicate which molecules fell within each node. Still further, the output may indicate an activity level of the molecules that fell within each node, whether individually per molecule or, more preferably, as an average or other statistical measure.

Additionally, for each node of the resulting tree structure, the output can preferably indicate the difference in activity level between the molecules in the node and the molecules in the node's parent. In a graphical representation of the tree structure, for instance, each node can be conveniently color coded to indicate, for example, whether it represents an increase or decrease in average activity as compared with its parent node. Such output is particularly valuable in the instance where a given parent node results in multiple children nodes that reflect different child-parent activity differentials. For example, if a parent node gives rise to three children nodes A, B and C, and node A reflects an activity increase while nodes B and C reflect activity decreases, then the output may readily indicate that the pharmacophoric mechanism used as a filter to create node A is the preferred mechanism.

An exemplary embodiment of the present invention can thus take a massive amount of data representing chemical compounds and convert that data into a tree structure that conveniently represents the foregoing and other valuable information. A chemist, who could not manually analyze such a vast amount of input data, can then readily analyze the organized information represented by the tree structure. The information generated by the invention can thus assist in the development of leads and in turn the development of beneficial new drugs.

In yet a further aspect, an exemplary embodiment of the present invention involves applying a tree structure generated in accordance with the invention in order to classify other compounds, so as to "virtually" determine what level of activity might be expected. Alternatively, in another aspect, an embodiment of the invention involves hierarchically clustering representations of chemical structures so as to generate a multi-domain chemical structure classifier, and then applying the classifier to identify pharmacologically useful classifications of test compounds. The test compounds could be compounds having unknown activity level, for instance.

Thus, in one respect, an embodiment of the invention can take the form of a method for screening a set of molecules (or for screening a data set representing a plurality of molecules), in order to assist in identifying sets of molecular features that are likely to correlate with specified activity. Each molecule has a feature characteristic and an activity characteristic. According to the method, the molecules are first grouped based on the similarity of their feature characteristics, and one or more of the groups are selected based on the activity characteristics of the molecules in the groups.

For each group, a common feature set is identified, and those molecules (one or more) that include the common feature set then form a new set of molecules. A decision is then made as to whether to repeat the process with respect to each such new set, and, if so, the method is repeated (grouping the molecules in the set, identifying a common feature set, etc.) In turn, the method involves providing as output a description of at least one of the new sets of molecules. The description preferably defines the common feature set of the set of molecules as well as the representative activity of the set of molecules. For a given set of molecules, the feature set and representative activity may thus establish a correlation between molecular features and molecular activity.

This method can be conducted with respect to a set of training data, which may be molecules that have been determined to have at least a designated activity characteristic, such as a minimum threshold level of measured activity. The activity characteristic may be unidimensional or multi-dimensional. Further, the process of selecting one or more of the groups of molecules can involve selecting groups that have at least a threshold concentration of a specified activity characteristic.

The process of grouping the molecules based on similarity of the feature characteristics of the molecules can involve establishing for each molecule a feature vector that is based on the feature characteristic of the molecule, and clustering the feature vectors of the molecules based on the similarity of the feature vectors. In turn, the process of clustering the feature vectors can involve applying a self-organizing-map. In that case, each group might be a cluster (or a metacluster) of the self-organizing-map. Alternatively, the process of clustering can involve application of any other algorithm, such as Wards clustering for instance.

The process of identifying a feature set common to the molecules in a given group can involve identifying a chemical substructure (at least part of a chemical structure, whether 2D or 3D in character) that is present in all of the molecules of the group. This chemical substructure can include an arrangement of atoms and bonds, which may be contiguous or non-contiguous. Further, identifying the common feature set could involve identifying a largest, or maximum, chemical substructure common to the molecules in the group.

A genetic algorithm (a genetic algorithm common substructure search, whether or not weighted) may be used to identify that largest common substructure. Alternatively, an exhaustive search (an exhaustive maximum common substructure search, whether or not weighted) can be made for all common substructures and then the largest can be selected from those identified. Still alternatively, the common substructure can be identified by comparing 2D or 3D physical relationships of the molecules in the group (e.g., by comparing graphs of the molecules, by comparing volume of overlap of 3D representations of the molecules, or by performing other such comparisons).

The output description provided can take the form of a tree structure that includes a root node and descendent nodes. The root node can reflect the data set and each descendent node can reflect a new data set (set of molecules) established during the process. Further, in addition to (or instead of) indicating a representative activity measure per set of molecules, the output could indicate an activity differential measure, indicating a change in activity level from parent to child.

In another respect, the method for screening a data set representing molecules can involve selecting from the data set at least one group of the molecules that have similar feature characteristics and that cooperatively represent a particular activity characteristic. Each such group may thus have a set of discriminating features that defines the similarity of the molecules in the group. For each such group, the method may then involve identifying at least one common subset of features of the molecules, based on a measure of how much the common subset participated in defining the discriminating features of the group. For each common subset of features, the method may then involve establishing a new data set that represents those molecules from the data set that include the common subset of features.

As with the first data set, the method may then involve selecting from the new data set at least one group of molecules that have similar feature characteristics and that cooperatively represent a particular activity characteristic. And as above, each such group has a set of discriminating features that defines the similarity of the molecules in said group. For each group thus selected, the method may then involve identifying at least one common subset of features of the molecules in the group, based at least in part on a measure of how much the common subset of features participated in defining the discriminating features of the group. Further, the method may further involve outputting data that indicates at least one of the common subsets of features.

In another respect, an embodiment of the invention can take the form of a computer-readable medium (such as a storage diskette, a memory, or the like) that embodies a set of machine language instructions executable by a computer processor to perform one or more of the various methods described above.

In yet another respect, an embodiment of the invention can take the form of a computerized method of converting a set of data representing a plurality of molecules into a data structure representing pharmacophoric mechanisms. The set of data might define respectively for each molecule both a structure and an activity characteristic. To start, a root node in the data storage medium can be established to represent the plurality of molecules.

The computerized method may then involve grouping the molecules of the root node into a plurality of groups based on structural similarity of the molecules. In turn, the method may involve selecting one or more of these groups based on the activity characteristics of the molecules in the groups. For each selected group, the method may involve identifying a common substructure among the molecules in the group. This common substructure, which will define a pharmacophoric mechanism, can take various forms such as a contiguous or non-contiguous structure of atoms and bonds for instance.

The computerized method may then involve, with respect to each identified common substructure, selecting from the root node that include one or more molecules that include the common substructure, and establishing a child node representing the one or more selected molecules. In turn, the method may involve deciding whether to expand the data structure from the child node. If so, the method may then recursively repeat the process, with the child node in place of the root node.

In the end, or during the process, the method may involve outputting an indication of at least a portion of the data structure, including an indication of at least one pharmacophoric mechanism developed in the process. The output may be a description of the data structure itself, and providing that output may include providing an output display such as a graphical display, a textual display, or a combination graphical-textual display, for presentation to a person such as a chemist.

Further, the output may include an description of one or more nodes of the data structure. This description can include information such as (i) an indication of the molecules represented by the node, (ii) the common substructure represented by the node, and (iii) an activity characteristic measure based on the activity characteristics of the molecules represented by the node. In addition, the output preferably includes a description of a child node that stems from a parent node, and the output provides an activity characteristic differential that represents a difference in activity level from the parent node to the child node. This differential may be shown by color coding on a graphical display, for instance.

In still another respect, an embodiment of the invention may take the form of a method for building a multi-domain molecular classifier. The method can involve receiving data representing a set of molecules and deriving one or more pharmacophores from the set of data. Each pharmacophore may define a node of a multi-domain classifier. The method may then involve using each pharmacophore respectively as a filter to establish a new set of data representing a subset of the molecules, such that each molecule in the subset includes the pharmacophore. In turn, the method may involve deriving one or more new pharmacophores from each new set of data, and each new pharmacophore can define a node of the multi-domain classifier. The result of this method is thus a classifier in the form of a tree structure having a number of nodes, where each node has as a filter a particular pharmacophore. One or more test molecules may then be fed through this tree structure, so as to classify the test molecules.

In still a further respect, an embodiment of the invention can take the form of a chemical structure classification method. The method may involve receiving into a computer a set of data that represents a training set of molecules, in which each molecule has a feature characteristic and an activity characteristic. The method may then involve using that training set of molecules to generate a chemical structure classifier by a process such as (but not limited to) those described above.

In turn, the method may involve applying the chemical structure classifier to classify given molecule (or a set of molecules) into multiple structural classes and providing as output an indication of the classes (classifications) into which the given molecule was classified. This output can serve as the basis for a presentation to a person such as a chemist, so as to conveniently inform the person of useful structural classes into which the given molecule fits.

The resulting chemical structure classifier may take the form of a phylogenetic-like tree structure that includes a number of nodes beginning with a root node. At least one of the nodes after (i.e., descending ultimately from) the root node has a corresponding feature set. In turn, the process of applying the classifier to classify a given molecule may involve filtering the given molecule through the tree-structure so that the molecule passes into a given node of the tree structure if the molecule contains the feature set corresponding to the given node. Viewed from another perspective, the process of applying the classifier can be considered to involve filtering a data-representation of the given molecule through the multi-domain classifier.

In yet another respect, an embodiment of the invention can take the form of a method of identifying multiple structural classes into which a given molecule fits. The method can involve representing each of a number of molecules by a respective structure characteristic that is keyed to a set of structural descriptors. For each molecule, the representation may take various forms, such as, for instance, a descriptor vector keyed to the structural descriptors, a 2D graph, or a 3D graph (e.g., involving spatial orientation (distances, angles, etc.) of portions of the molecule, volumes of overlap, or the like). The structural descriptors can also take any form, such as, for instance, MACCS keys, BCI keys, or Daylight fingerprint keys.

In turn, the method can include hierarchically clustering representations (e.g., data representations) of the molecules based on the molecules' respective structure characteristics, so as to establish a hierarchical tree structure. The hierarchical clustering process can take any of a variety of forms, including, for instance, agglomerative clustering and divisive clustering. Further, the clustering process may involve evaluating similarities between molecules. This evaluation may involve a comparison of descriptor vectors, which may involve computing distances such as Euclidean distances, Tanimoto distances, Tversky coefficients, Euclidean-Soergel products, and/or Euclidean-Tanimoto products, for instance. Alternatively, the evaluation may involve a comparison of physical molecular properties, such as 3D volumes, molecular force field shapes, and other spatial distributions of molecular properties. The tree structure would be made up of a number of nodes, each of which would represent at least one molecule.

For some or all nodes of the tree structure, either as an integral part of the process of creating the tree structure (e.g., the node) or after some or all of the tree structure is created, the method may involve identifying a respective chemical feature (or feature set) common to the molecule(s) represented by the node. This chemical feature may be a 2D substructure (molecular subgraph) or a 3D substructure (3D pharmacophore or spatial arrangement of molecular features) that is suitably (e.g., within some range or tolerance) similar to an arrangement of 3D substructure that exists in each molecule represented by the node. (A 3D substructure can be said to be contained or included within a molecule if the 3D substructure can be rotated or translated in three dimensions such that each component of the substructure maps to a similar component within the molecule to a given tolerance.) For purposes of this description, the term "substructure" may be used in place of the term "feature" or "feature set" or vice versa.

At least two of the identified chemical substructures will be different than the structural descriptors that formed the basis for the initial characterizations of the molecules. In other words, at least two (and preferably many more) of the identified chemical structures will be newly learned substructure keys.

The method may then involve filtering a representation of the given molecule through the hierarchical tree structure. The representation of the given molecule would thereby fall within a number of nodes of the tree descending from the root node, to the extent the molecule includes the chemical substructures identified for those nodes.

In turn, the method may involve providing as output an indication of the nodes into which the given molecule falls including an indication of the chemical substructure identified for each node into which the given molecule falls. The chemical substructure identified for each such node will thus define a structural class into which the given molecule fits. And this information may be usefully provided as output to a chemist or other person.

The foregoing as well as other advantages and features of the present invention will be understood by those of ordinary skill in the art by reading the following detailed description with reference where appropriate to the accompanying drawings.

BRIEF DESCRIPTION OF THE DRAWINGS

Exemplary embodiments of the present invention are described herein with reference to the drawings, in which:

FIG. 3 (four parts) is a table listing an illustrative set of descriptors for use in an embodiment of the present invention;

DETAILED DESCRIPTION OF EXEMPLARY EMBODIMENTS

Figure 1:
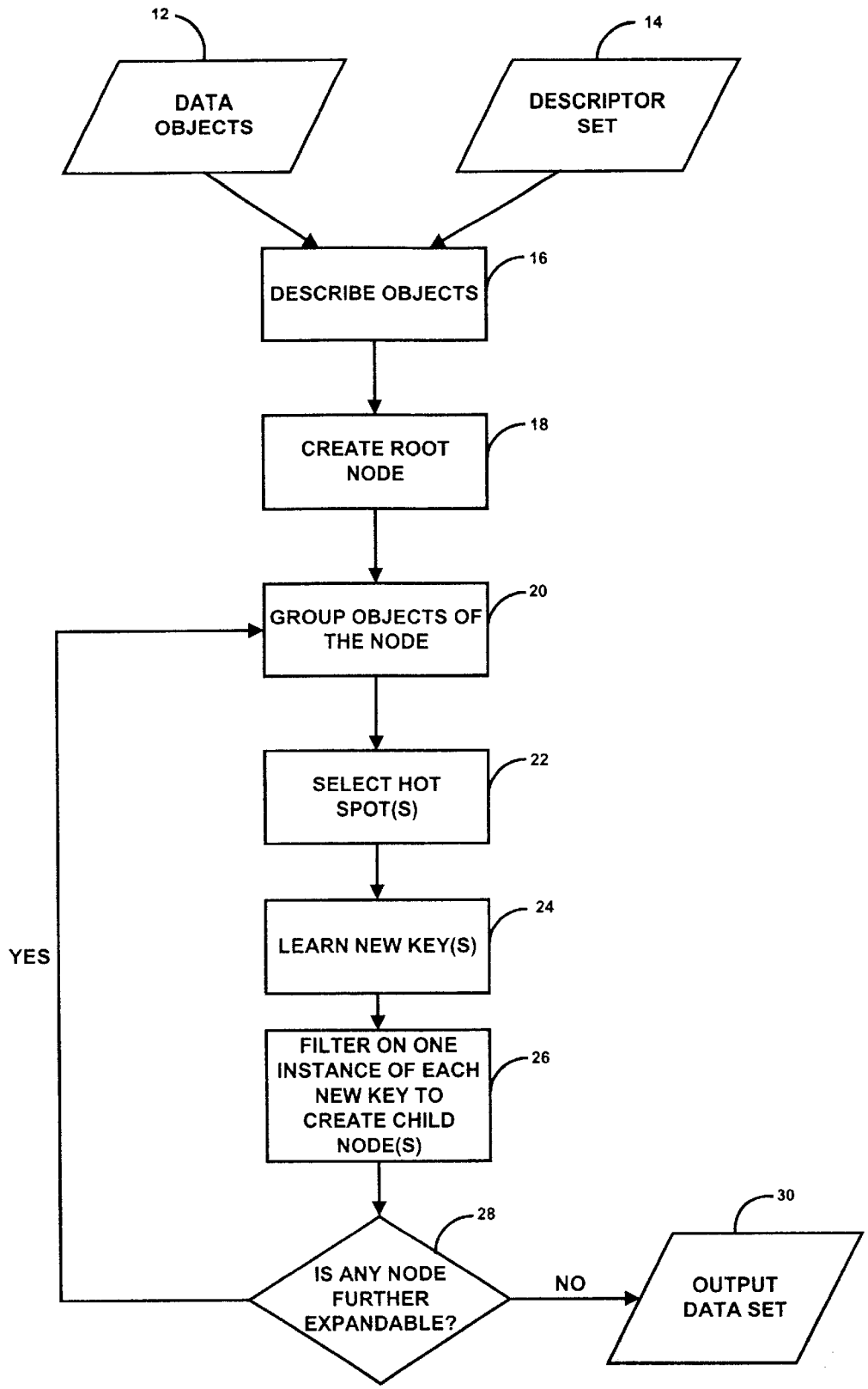
FIG. 1 is a flow chart depicting an exemplary set of functions that a computer may perform according to an embodiment of the present invention.

As indicated above, the present invention can take the form of a computer-based system for the automated analysis of a data set. The system is configured to correlate features with responses and to thereby identify or discover scientifically useful subclasses of features or mechanism models, namely, features that are likely to correspond to observed or predicted responses.

An exemplary embodiment of the invention provides a computer-based system for generating structural subclasses that relate to pharmacophoric activity and thereby generating a hierarchical tree-structure that embodies rules or processes for creating scientifically useful pharmacophoric mechanisms. Another exemplary embodiment provides a computer-based system for generating a multi-domain classification of chemical structures, by creating a hierarchical tree-structure, whose nodes each define a chemical substructure, and then filtering a set of chemical structures (e.g., molecular representations) through the tree so as to classify the chemical structures.

Those of ordinary skill in the art of data mining and artificial intelligence will appreciate from reading this description, however, that there are numerous other practical applications for the invention, and additional applications may be developed in the future. Therefore, the invention may extend both generally to other applications as well as specifically to particular applications in chemistry and biology.

The functional steps described herein are preferably encoded in a set of machine language instructions (e.g., source code compiled into object code), which are stored in a computer memory or other storage medium (e.g., a computer disk or tape) and executed by a general purpose computer. (Alternatively, the functional steps may be carried out by appropriately configured circuitry, or by any combination of hardware, software and firmware.) The present invention may thus take the form of a computer-based system, which itself may comprise, for example, (i) a method for performing a plurality of functional steps, (ii) a computer readable medium (such as a disk, tape or other storage device) containing a set of encoded machine language instructions executable by a computer processor for performing a plurality of functional steps, and/or (iii) a machine (such as a general purpose digital computer) programmed with a set of machine language instructions for carrying out a plurality of functional steps (in the recited order or in a varied order). Provided with this disclosure, those of ordinary skill in the art will be able to readily prepare a suitable set of instructions for performing these functions and to configure a general purpose computer to operate the instructions.

1. Generating Phylogenetic-Like Trees

In accordance with an exemplary embodiment, there is provided a computer-based system for generating pharmacophoric subclasses through multi-domain clustering and for thereby generating tree structures that embody subclass definitions scientifically correlated with observed or predicted activity.

Tree structures referred to as "phylogenetic trees" are commonly used in tracing evolutionary history of living organisms, in tracing the history and development of languages, and in other areas. In biology, for instance, branch points in phylogenetic trees are based on commonly held features of the set of organisms which help categorize them in a certain way, e.g., warm-blooded or not; 5-, 7-, or 9-lobed leaves; etc.). Organizing sets of organisms into a tree allows quick categorization of new unknown individuals. At the genetic level, phylogenetic trees are used to hypothesize individual gene mutations and evolution over time of a particular piece of genetic code. The tree can then be used to postulate how closely or distantly related two sequences are, by the number of branches in the tree as well as the length of each limb.

Referring to the drawings, FIG. 1 is a flow chart illustrating an exemplary set of functions that a computer may perform according to an embodiment of the present invention. It will be appreciated that a computer-system may be readily programmed to execute an appropriate set of machine languages instructions designed to carry out some or all of these functions as well as other functions if desired.

As shown in FIG. 1, at block 12, a computer may receive as input or otherwise be programmed with a set of data representing a plurality of data objects, each of which may respectively have features and a response characteristic. The response characteristic of each data object may be one dimensional or multi-dimensional. At block 14, the computer may also receive as input or otherwise be programmed with an initial set of descriptors or "keys" that can be used to define a particular pattern (subgraph) in a data object (graph). Each of these keys may be weighted to indicate the relative importance of the keys, as defined by an expert and/or through computer analysis for instance. The data sets referenced at blocks 12 and 14 may alternatively be a single data set.

At block 16, the computer may then establish a description of each object based on a comparison of the features of the object with the set of keys. The description for each object may take any desired form. By way of example and without limitation, the description for each object may take the form of a descriptor vector (e.g., bit string), each element of which may be a binary indication of whether a corresponding one of the keys in the key set is present or absent in the data object. Each descriptor vector may thus be the length of the key set. Alternatively, it is appreciated that the description may indicate expressly only which descriptors are present, thus implicitly indicating the absence of other descriptors. Further alternatively, rather than having the computer generate a description for each data object, the input data set may instead include pre-established descriptions for each data object.

At step 18, the computer next preferably creates an initial "root" node of the tree structure. The root node may contain representations of all or a subset of the data objects. Each representation may, for instance, be an ID number that corresponds to a stored record for the data object (thereby correlating with the descriptor vector and response characteristic of the data object).

As presently contemplated, with respect to the data objects in the node, the computer may then select one or more groups of the data objects, each group preferably consisting of objects that have similar feature descriptions and that are characterized by a specified response characteristic (e.g., level of a specified response). Any statistical or other mechanism may be used to group the objects for this purpose. For example, the computer may group the objects according to their feature similarity (as embodied in the descriptions established for each object) and then select those groups whose objects exhibit the specified response characteristic. Alternatively, for example, the computer may simultaneously group the objects along both feature and response dimensions, as for instance using stepwise linear regression. Blocks 20 and 22 illustrate the first of these examples.

Referring to block 20, the computer may group the data objects of the node according to similarity of their descriptor vectors. This function may thus involve grouping the descriptor vectors of the data objects according to their similarity. Those skilled in the art are familiar with numerous computer-based methods for grouping such vectors, any of which can be applied at this stage. As presently contemplated, a exemplary method of grouping the vectors may most beneficially provide neighborhood information, in the form of localized groups of vectors, such that the grouping evidences similar groups as well as similar vectors within each group. An example of one such suitable grouping method is clustering, such as provided for instance by the well known Kohonen Self-Organizing Map (SOM). Of course, other examples of grouping (and, more particularly, clustering) exist as well.

At block 22, the computer may then identify one or more groups whose data objects have a particular or sufficient concentration of the specified response. If, at block 20, the computer performed SOM clustering based on the object descriptions, then, at block 22, the analysis may involve identifying a cluster or neighborhood of clusters that have a sufficient concentration of the specified response characteristic. The determination of what constitutes a sufficient concentration of the specified response characteristic is a matter of design choice. By way of example, the determination may be based on the percentage and/or number of objects in the group that have the specified response characteristic and/or the absence from the group of objects that have a particular response characteristic (such as a characteristic contrary to that specified). The computer may designate each such selected group (one or more) as a "hot spot."

In an exemplary embodiment, each hot spot may have a set of discriminating features defining the feature-similarity of objects in the group. Reasonably assuming that the objects are not all identical, this set of discriminating features will not describe all of the objects in the selected group but may instead represent a closest fit or closest match to the descriptions of the objects in the group. In a trained SOM map, for instance, each cluster typically defines a template or vector of weighted keys, which is a closest fit or closest match for the descriptor vectors of the objects in the cluster. If the hot spot is a single cluster, the template of the single cluster may thus define the discriminating features of the hot spot. Alternatively, if the hot spot is a neighborhood of clusters, the template of a core cluster or some function of the templates of all clusters in the neighborhood may define the discriminating features.

At block 24, the computer may next advantageously learn one or more new keys from each hot spot. To do so, as presently contemplated, the computer may actively map the discriminating features of the hot spot back to the data objects in the hot spot, so as to discover what features or components (i.e., aspects) of the objects contributed most extensively to the similarity of the objects (i.e., what it is about the objects that caused the statistical analysis to group the objects together). By way of example, and without limitation, the computer may score the features or components of each data object based on the number of times the features or components participate in matching the discriminating features of the hot spot. The computer may then search for a subset of features or components that is common to the objects in the hot spot and that has one of the highest composite scores (e.g., averaged among the objects in the hot spot).

Since each hot spot is generated based on concentration of response characteristic, it is reasonable to conclude that the common subset of features, and particularly the maximum common subset of features, in a given hot spot is likely to be responsible for the response characteristic exhibited by objects in the hot spot. Therefore, the computer may deem at least the maximum common subset of features to be a mechanism model for achieving the specified response. This mechanism model may be considered a new key, since, like the keys initially received at block 14, the mechanism model can be used to describe one or more aspects of a data object.

At block 26, the computer may next apply the newly learned keys as filters to grow child nodes in the tree. In particular, with respect to each new key, the computer may create a new subset of data objects by filtering all of the data objects in the node through a filter defined by the key. All of the data objects that match the key will pass through the filter, thereby creating a child node. Further, advantageously, to the extent a data object matches more than one of the learned keys, it may fall into multiple children nodes at once (thereby resulting in a multi-domain classification).

Once the computer has grown one or more new children nodes in the tree structure, the computer may review the "leaf" nodes (i.e., terminal nodes) in the tree to determine which nodes to explore further and which node to explore next. The computer may apply any of a variety of rules to determine which node to explore next. As examples, the computer can grow the tree in a depth-first manner, by exploring an entire branch before returning to explore the closest ancestor node. Alternatively, the computer can grow the tree in a breadth-first manner, by filtering on all keys at a given level of the tree (i.e., all nodes of a particular generation) before proceeding down to the next level of the tree.

Thus, at block 28, the computer may then determine whether a given node of the tree is further expandable, that is, whether additional information of interest can be gleaned from further expanding the branch. If the node is to be expanded further, the computer then repeats the process from block 20 with respect to that node, grouping objects, selecting hot spots, learning one or more new keys, and so forth.

Once no more nodes or branches of the tree are further expandable (i.e., once a determination is made that no further useful information will be gleaned), at block 30, the computer may provide an output. As described above, the output may be a description of all or part of the tree structure. For example, the output can be a graphical, or text or data based description of the various nodes and branches (links between nodes). For each node (other than the root node), the output can indicate the learned key that gave rise to the node. Further, for each node, the output can provide an indication of which data objects fell within the node and a representative response characteristic.

2. Generating Phylogenetic-Like Trees Embodying SAR Information

Figure 2:
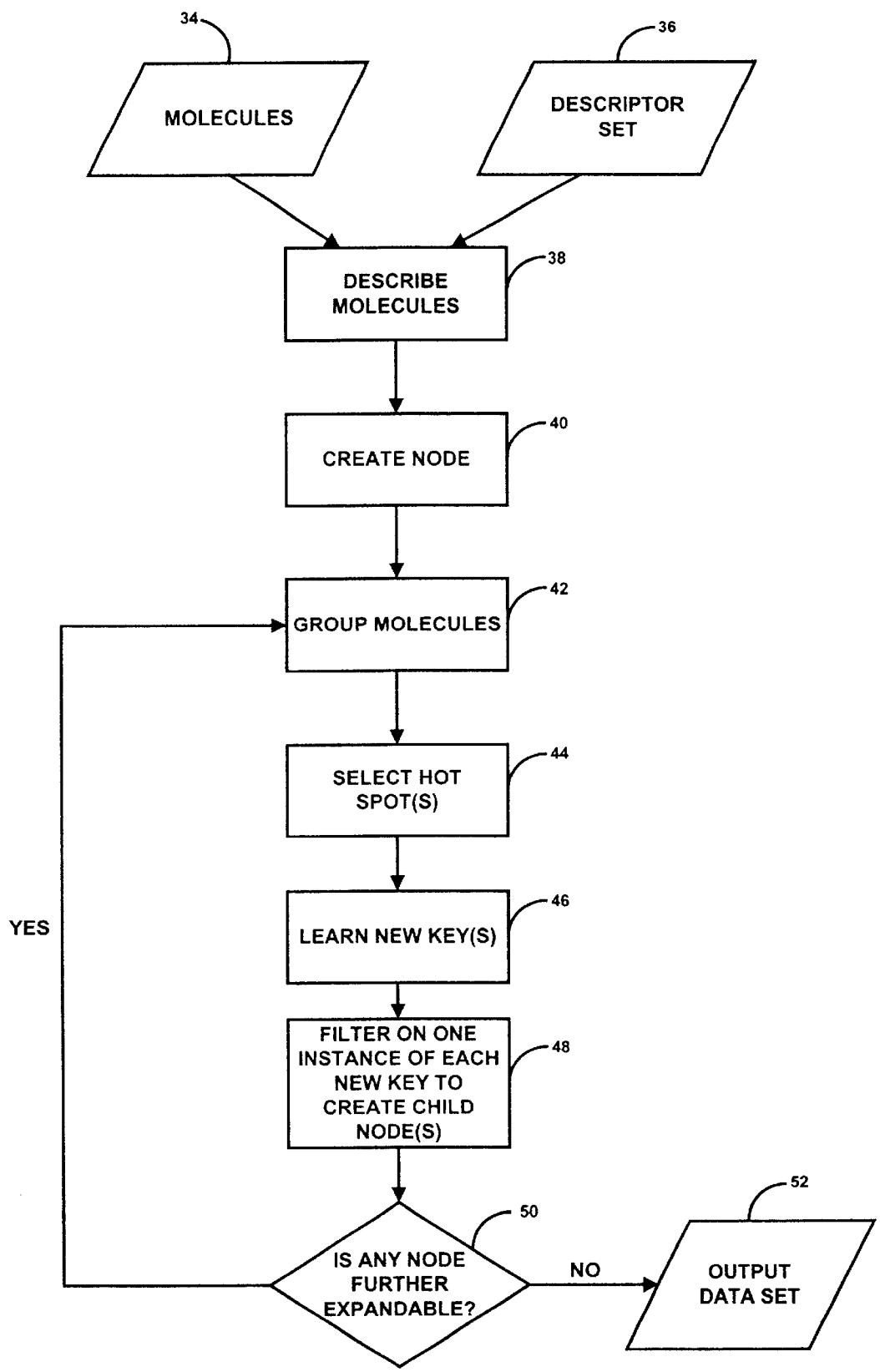
FIG. 2 is a flow chart illustrating an exemplary set of functions that a computer may perform to analyze chemical structure-activity relationships according to an embodiment of the present invention.

A more particular exemplary embodiment of the invention will now be described in the context of chemical SAR analysis and the development of phylogenetic-like tree structures representing pharmacophoric mechanism models. Referring to the drawings, FIG. 2 provides an overview of an exemplary set of functions that a computer may perform according to this exemplary embodiment. As in the generalized embodiment described above, it will be appreciated that a computer-system may embody some or all of these functions as well as other desired functions.

An overview of these functions will first be provided, and each function will then be described in more depth so as to enable one of ordinary skill in the art to practice the invention as presently contemplated. In this regard, it will be appreciated that the details of these functions may be extended by analogy to the generalized analysis above, and vice versa. Further, it should be understood that variations to the routines described herein, and the order of the routines, are possible.

a. Overview

As shown in FIG. 2, at block 34, the computer may receive or be programmed with a set of digital data representing molecules and their respective response characteristics. This description will focus on activity as an example of a molecular response characteristic. However, it should be appreciated that, instead of activity (or in addition to activity), the response characteristic can take a variety of other forms. By way of example (and without limitation), the response characteristic can generally be any chemical, physical and/or biolgical property. Examples of chemical and physical properties include measures of electrophilicity, measures of solubility, measures of logP, measures of pKa, numbers of hydrogen bond donors, number of hydrogen bond acceptors, number of rotatable bonds, and molecular weight. Examples of biological properties include measures of interaction with biological systems.

At block 36, the computer may also receive or be programmed with a set of digital data representing an initial set of descriptors or "keys" that may define a particular pattern (subgraph) in a molecule (graph). These patterns preferably relate to physical chemical properties such as atoms, bonds, shapes, sizes, orientations, etc. (hereafter referred to generally as "structure"). Therefore, these keys may also be referred to as "substructure keys", "substructure descriptors" or the like.

At block 38, the computer may establish a description for each molecule. By way of example, the computer may determine with respect to each molecule whether each substructure key is present or absent and may thereby generate a descriptor vector for each molecule. At block 40, the computer may establish a root node for the tree structure to be created. At block 42, the computer may then perform a statistical analysis to group all or a subset of the molecules according to the similarity of their descriptions, possibly along dimensions related to their respective activity levels, and preferably in a fashion that provides neighborhood information such as with SOM clustering.

At block 44, the computer may identify one or more groups of structurally similar molecules (e.g., clusters or neighborhoods in the SOM grid) that have a sufficient concentration of active molecules, and the computer may designate each such group as a hot spot. At block 46, the computer may adaptively learn one or more new substructure keys from each hot spot, by actively mapping the discriminating features of the hot spot back to the molecules in the hot spot, so as to determine what structural similarity it is that is useful (i.e., to determine what the statistical grouping-analysis learned about the molecules).

At block 50, with respect to each new key, the computer may next grow the tree by filtering the molecules of the current node through a filter defined by the new key. As a result, the computer establishes one or more children nodes, each representing a number of molecules from the parent node that include the respective learned key. If a given molecule in the parent node includes more than one of the learned keys, the molecule will fall within more than one child node.

At block 52, the computer may evaluate the "leaf" nodes of the tree to determine whether any node should be further expanded and which node to explore next. As noted above, the computer may grow the tree in a breadth-first manner, a depth-first manner, or according to other rules as desired. If a node is to be expanded further, the computer then repeats the process at block 42 with respect to the molecules in that node. When the computer finishes growing the tree, the computer may then provide as output a data set in the form of a tree structure, for instance, advantageously representing structural families of compounds and SAR information.

b. Functional Blocks i. Receiving Data

According to an exemplary embodiment, the computer preferably receives or is programmed with a data set representing molecules and their respective activity levels (i.e., potencies or responses). This data set may result from combinatorial chemistry and/or high throughput screening techniques, or from any other source.

Each molecule is preferably represented by an ASCII string or any other suitable representation that can be computer processed. (Any data string representing a molecule may be referred to as a "molecule data string.") By way of example and without limitation, a useful system for representing chemical molecules in ASCII form is provided by Daylight Chemical Information Systems, Inc., of Irvine, Calif. Daylight establishes a language that it terms "SMILES" (Simplified Molecular Input Line Entry System), which contains the same information about a molecule that would be found in an extended connection table but sets forth the molecule as a linguistic construct rather than as a data structure. Examples of SMILES strings include:

ethane: CC
carbon dioxide: O=C=O
hydrogen cyanide: C#N
triethyl amine: CCN(CC)CC
acetic acid: CC(=O)O
cyclohexane: C1CCCCC1
benzene: c1ccccc1

A unique molecule may be represented by more than one SMILES string. For example, $N^2$isopropyl benzoylhydrazide may be represented by both the string "c1ccccc1C(=O)NNC(C)C" and the string "CC(C)NNC(c1ccccc1)=O". The Daylight program therefore generates a connection table, which maps the exact structure of each molecule, in terms of atoms and their bond connections, from various possible representations of the molecule.

As indicated by Daylight, SMILES strings provide a compact, human understandable and machine readable representation of molecules, which can be used for artificial intelligence or expert systems in chemistry. Other information about the creation and use of SMILES strings is readily accessible at Daylight's world wide web site, which is located at http://www.daylight.com, and the reader is directed to the Daylight web site for more detailed information. In addition, further information about SMILES strings is provided in the Journal of Chemical Information and Computer Science, 1988, 28, 31–36.

The molecule representations may be provided in the same or a separate data set as the activity information. For example, a single data file or database may contain separate entries or records for each molecule, including as separate fields (i) a bit string molecule identifier and (ii) a bit string activity identifier. Alternatively, separate data files or databases (or separate tables) may be provided for the molecules and for empirical data gathered with respect to the molecules in one or more assays. In a preferred embodiment, each molecule will be represented by a unique molecule ID (e.g., a database record number), for convenient reference.

The activity information for a molecule may take any suitable form. By way of example and without limitation, the activity information may be an absolute measure of activity of the molecule in an assay or may be a measure of activity relative to the average activity of all molecules tested in an assay. For instance, a molecule may be tested at various levels of concentration, a curve fit to the concentration vs. activity points, and the concentration necessary to cause half of the maximum activity determined. The activity information for the molecule may then be the resulting $IC_{50}$ concentration.

Further, the activity information for a molecule may be one-dimensional or multi-dimensional. For instance, the activity may be a single measurement of whether or how well the molecule bound to a particular protein in an assay. This measurement may be indicated, for instance, by an integer (such as a rank between 0 and 3, where 0 indicates inactivity and 3 indicates the highest relative level of activity) or by a Boolean value (where "true" indicates activity and "false" indicates inactivity). Alternatively, the activity may be multi-dimensional, such as an indication of how the molecule performed in various aspects of a single assay or multiple assays. Such multi-dimensional activity information for a molecule may be represented by a vector, for instance, whose members indicate activity levels of the molecule for a plurality of assays. In any event, the activity information for each molecule is preferably encoded in a format suitable for computer processing, such as in a bit string.

In addition, the computer preferably receives or is programmed with a set of substructure descriptors keys, which can serve to represent aspects of chemical molecules. Each key may be any property that can define a physical aspect of a chemical molecule. By way of example and without limitation, the keys may specify atoms, atom pairs, proton donor-acceptor pairs, other groupings, aromatic rings, characteristics of atoms or sets of atoms (e.g., hydorgen bond affinity, location of electron density, etc.), shapes, sizes and/or orientations. Further, the keys may define 2-D representations (such as atom pairs, bonds and aromatic rings, for example) or 3-D representations (such as a distance between chemical components having variable orientation, an indication of component orientation, a volume of overlap, a distance between atoms, etc.) Thus, unless otherwise restricted, the term "substructure" is not necessarily limited to 2-D structural features such as atoms and bonds but can extend more broadly to other physical characteristics.

Each substructure key may be weighted to indicate the relative importance of the key in describing two molecules that are similar. By way of example, these weights may be pre-established (e.g., by a chemist) based on a statistical measurement of how "unusual" it is to find the substructure in a population of molecules; the more unusual the substructure, the more similar are molecules that share the substructure, and so the more highly weighted the key. A different procedure may be used to establish weights for newly learned keys, as will be described in more detail below.

Each substructure key is preferably represented by an ASCII string or any other suitable representation that can be computer processed. (Any data string that represents a descriptor may be referred to as a "descriptor data string.") By way of example and without limitation, a useful system for representing chemical molecules in ASCII form is also provided by Daylight Chemical Information Systems, Inc. Daylight establishes a language called "SMARTS," which can be used to specify substructures using rules that are straightforward extensions of SMILES strings. Additional information about Daylight SMARTS keys is provided at the Daylight web site indicated above.

According to Daylight, both SMILES and SMARTS strings employ atoms and bonds as fundamental symbols, which can be used to specify the nodes and edges of a molecule's graph and assign labels to the components of the graph. SMARTS strings are interpreted as patterns that can be matched against SMILES string representations of molecules, in the form of database queries for instance. Other examples of substructure representations include "MACCS" keys (i.e., fragment-based keys for use in describing molecules, where MACCS stands for "the Molecular ACCess System) and other keys as defined by MDL Information Systems, Inc., for instance. (For additional information about the keys established by MDL, the reader is directed to MDL's web site, at http://www.mdli.com.)

The set of substructure keys may be of any desired size, and the keys may take any desired form. In an exemplary embodiment, however, the computer uses a set of keys specified in the SMARTS language to emulate 157 of the MACCS keys defined by MDL, which have been selected to provide structural descriptions of molecules and to thereby facilitate improved correlation of structure and activity. FIG. 3 provides a table of these 157 keys as SMARTS string representations and lists for each key an optional weight and a corresponding MDL MACCS definition. Of course, it will be appreciated that other key definitions and forms of keys can be used instead, depending on the features of interest being studied for instance.

ii. Establishing Descriptor-Vectors

The computer preferably establishes a description of each molecule based on the set of substructure keys. In an exemplary embodiment, without limitation, the description for each molecule may take the form of a descriptor-vector, whose elements indicate whether respective keys in the substructure key set are present or absent in the molecule (i.e., whether the respective substructures are present or absent). If the molecules are represented by SMILES strings and the keys are represented by SMARTS strings, the computer can readily determine whether a key is present in a molecule by querying the corresponding SMARTS string against the corresponding SMILES string (and more particularly the Daylight connection table).

The members of the descriptor vector for a molecule may be values reflecting the weights of the keys that are present in the molecule. By way of example, for each key that is present in a molecule, the corresponding member of the descriptor vector for the molecule may be the weight of the key, and, for each key that is absent, the corresponding member of the descriptor vector may be zero. For instance, if a key has a weight of 5 and the computer deems the key to be present in a molecule, then the computer may assign a value of 5 to the corresponding element of the descriptor vector for the molecule. On the other hand, if the computer deems the key to be absent from the molecule, then the computer may assign a value of 0 to the corresponding vector element.

Alternatively or additionally, as in the exemplary embodiment, each member of the descriptor vector for a molecule may simply reflect the presence or absence of the key in the molecule. In this regard, the value of each member of the descriptor vector may be a binary weight (e.g., 0 or 1), and the descriptor vector may take the form of a simple bit string. This arrangement is of course useful where the descriptors themselves are not weighted. Further, this arrangement is useful where the computer maintains the weights of the keys in a separate file or table for instance so that the weights are associated by reference with the respective (non-zero) elements of each descriptor vector.

In an exemplary embodiment, the computer may require each key to appear at least a predetermined number of times in the molecule at issue in order for the key to be deemed "present" in the molecule. The predetermined number of times is a matter of design choice and may vary per key. By way of example, column 2 of FIG. 3 lists for each key a minimum number of hits that can be required in order to deem the respective key to be present in a molecule. Referring to this column for instance, exemplary key 134 is shown to have a minimum number of hits of 2 (for example), so the computer should find at least two nitrogen atoms in a molecule in order to deem the key to be present in the molecule. Of course, other values can be used instead.

Figure 4:
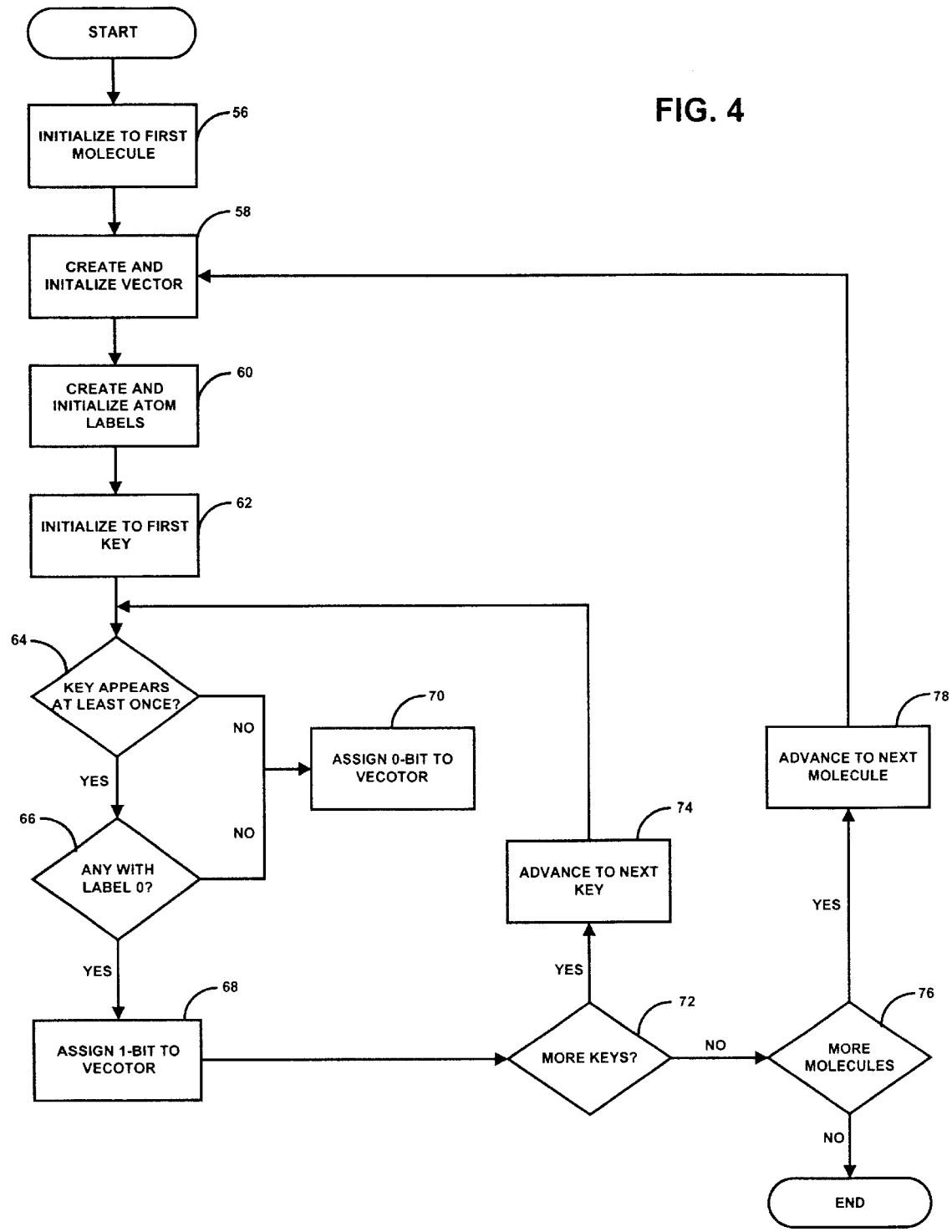
FIG. 4 is a flow chart illustrating an exemplary set of functions that a computer may perform to generate descriptor vectors according to an embodiment of the present invention.

Referring to the drawings, FIG. 4 illustrates an exemplary set of functional blocks that may be involved in establishing descriptor-vectors. In this example, at block 56, the computer may initialize a pointer (e.g., counter) to the first molecule (SMILES string). For the given molecule, at block 58, the computer may create a descriptor vector of a length corresponding to the number of keys (157 in the present example), and initialize each member of the vector to zero. In addition, at block 60, the computer may establish a label for each component (e.g., each atom) in the molecule, which the computer will subsequently use to indicate whether the atom has participated in matching a substructure key, and in turn to determine whether a key is wholly subsumed in the molecule by another key. The computer may initialize the label for each component to a value of zero, indicating that the component has not yet participated in matching a substructure key.

At block 62, the computer may then initialize a pointer to the first substructure key (SMARTS string). At block 64, the computer may then search the connection table associated with the SMILES depiction of the molecule to determine whether the key appears at least once (or, alternatively, at least a designated minimum number of times) in the molecule. If so, then, at block 66, the computer may determine whether at least one component (e.g., atom) in the molecule that participated in matching the key has a label set to 0. If so, then at block 68, the computer may assign a binary 1 value to the corresponding member of the vector. However, if the computer determines that the key does not appear at least once (or at least the designated minimum number of times) in the molecule or that the labels for all components that participated in matching the key are set to 1, then, at block 70 the computer may assign a binary 0 value to the corresponding vector member.

In turn, at block 72, the computer may determine whether additional keys exist. If so, then, at block 74, the computer may advance to the next key and return to block 64. If not, then, at block 76, the computer may determine whether additional molecules exist. If so, then, at block 78, the computer may advance to the next molecule and return to block 58. If no additional molecules exist, then the computer may conclude that it has finished establishing descriptor vectors for at least the present iteration.

Of course, variations to this and other exemplary routines described herein are possible. For instance, when establishing descriptions, the computer may deem to be absent from a molecule any substructure key that is wholly subsumed by another substructure key.

iii. Initializing the Tree Structure

Once the computer has received the input data set, the computer may begin establishing the phylogenetic-like tree structure by first setting aside memory space for the tree structure and then creating a root node representing a plurality of molecules. From this root node, the computer will then generate descendent nodes that may each represent one or more molecules and that may each define a commercially valuable pharmacophoric mechanism.

A training set of molecules is preferably used to build the tree structure and therefore defines the set of molecules to be represented by the root node. This training set could be all or a subset of the molecules under analysis. In an exemplary embodiment, the training set is all of the active molecules in the input data set, and none of the inactive molecules. A molecule may be deemed to be active for this purpose according to any desired criteria. By way of example, a molecule may be deemed to be active if its activity level exceeds some predetermined level or is non-zero. As another example, if the activity characteristic of each molecule is multi-dimensional, then a molecule may be deemed to be active if the molecule is active with respect to each of a set of assays (various dimensions of the activity characteristic). In other words, a molecule may be deemed to be active if the molecule has some desired set of activity characteristics in a multi-dimensional representation of active (for example, active along all dimensions or active along some dimensions and inactive along others, etc).

This training set of active molecules advantageously enables the computer to learn what makes the active molecules similar to each other. The inactive molecules could then be used subsequently for testing. Alternatively, the training set can be a subset (sample) of the active molecules, and the remaining active molecules could be used subsequently for testing. Still alternatively, any other training set can be used.

Beginning with the root node, each node of the tree structure may take the form in memory of an object with attributes. In the present example, these attributes include, for instance, (i) a "node ID" attribute, (ii) an "actives" attribute, (iii) a "status" attribute, (iv) a "key" attribute, and (iv) a "learned keys" attribute. The "node ID" attribute uniquely identifies the node in the tree structure. In the exemplary embodiment, nodes are numbered with consecutive integers beginning with 0 for the root node, 1 for the first child, and so forth. The "actives" attribute is a list of the molecules represented by the node, preferably by reference to the molecule IDs, which then correlate with a stored indication of the respective descriptor vectors and activity characteristics for the molecules. The "status" attribute may define a state of node., such as whether the node has been processed (e.g., explored) already or whether the node should not be processed (e.g., because the node is a duplicate of another node that was already explored). The "key" attribute may, in turn, define a chemical feature set or filter that gave rise to the node, as will be described more below. Further, the "learned keys" attribute may be a list of keys that the computer learns from its analysis of the molecules in the node, as will also be described more below.

Figure 5:
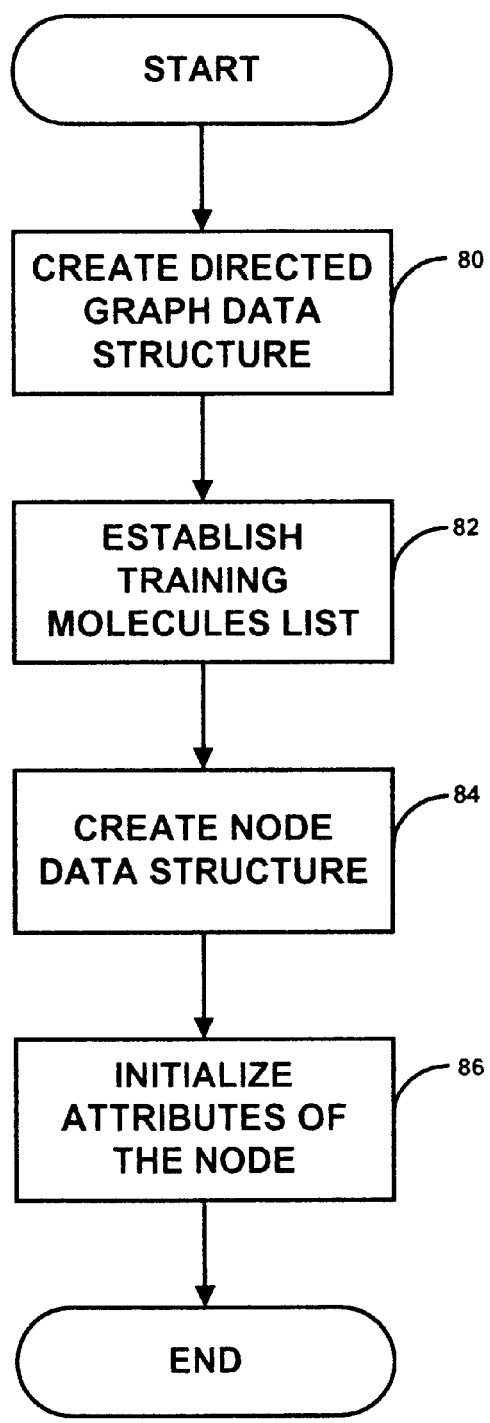
FIG. 5 is a flow chart depicting an exemplary set of functions that a computer may perform to initialize a tree structure and root node structure according to an embodiment of the present invention.

FIG. 5 illustrates a set of functional blocks that may be involved in initializing the tree structure and establishing the root node. As shown in FIG. 5, at block 80, the computer creates a directed graph (tree) data structure, by reserving a portion of memory. At block 82, the computer then establishes a training-molecules list, which, in the exemplary embodiment, may be a list of the molecule IDs of all active molecules represented by the input data set. At block 84, the computer then establishes a node of the graph (which could, for instance, be a database record). In turn, at block 86, the computer initializes attributes of the node to make it the root node, setting the "node ID" attribute to 0 and the "actives" attribute to the training-molecules list established at block 82. Since the root node is not established by filtering from another node, the computer may set the "key" attribute of the root node to 0 or null. In addition, to start, the computer has not yet learned any new keys from the root node, so the computer may set the "learned keys" attribute of the root node to 0 or null as well.

As noted above, the order of routines described herein can be varied. As an example, the computer can establish the training-molecules list (e.g., list of actives) before it establishes descriptor vectors for the molecules. The computer may then conveniently establish descriptor vectors for only the molecules of the training set. On the other hand, to the extent the other molecules (e.g., inactives) will be used to test the completed tree structure or for other purposes, it may be worthwhile establishing descriptor vectors for all of the molecules at once.

iv. Grouping Molecules

Having generated a node representing a plurality of molecules, the computer then begins processing of the data to establish pharmacophoric mechanisms. To start, the computer preferably identifies one or more groups of structurally similar molecules that have (i.e., that represent or exhibit) a high concentration of activity (e.g., a high percentage of active molecules—or other response characteristic at issue). As noted above, numerous mechanisms exist to establish such correlations between structure and activity, and any of these methods may be suitably employed at this stage. In an illustrative embodiment, however, the computer may first group the molecules according to similarity of their structural descriptions and then select one or more groups of structurally similar molecules that also have a high concentration of activity.

An exemplary method of grouping molecules according to their structural similarity is clustering. Numerous clustering techniques are known to those skilled in the art and can be employed at this stage of the process. Some general examples of clustering techniques include 2-D SOM clustering, agglomerative clustering (e.g., Wards, complete link, average link, single link, or centroid) and divisive clustering (e.g., recursive partitioning (such as described in the background section above), the DIANA algorithm, or the MONA algorithm). Various such clustering methods (such as agglomerative or divisive clustering) may involve making comparisons between entities so as to group the most similar entities together. Such similarity evaluations can involve computing Euclidean distances, Tanimoto distances, Tversky coefficients, Euclidean-Soergel products, Euclidean-Tanimoto products, or other measures.

Further, while clustering methods typically produce clusters, a group of molecules selected at this stage in the process can be either one such clusters or a number of such clusters or "metacluster." Examples of methods known in the art for metaclustering include the Kelley method, the point-biserial method, Hubert's Gamma method, and Fagan's method.

An exemplary embodiment applies 2-D SOM clustering (possibly with metaclustering) at this stage in the process. The structure and operation of SOM clustering mechanisms is well known to those skilled in the art and an example is described, for instance, in T. Kohonen, Self-Organizing Maps (Springer Verlag, Berlin Heidelberg 1995, 1997), the entirety of which is hereby incorporated herein by reference. Other clustering methods suitable for use herein are also described, for instance, in Geoffrey Downs et al., "Similarity Searching and Clustering of Chemical-Structure Databases Using Molecular Property Data" (Krebs Institute, 1994), and R. Dubes and A. K. Jain, "Clustering Methodologies in Exploratory Data Analysis," Advances in Computers, Volume 19, pages 113–128 (Academic Press, New York, 1980), the entirety of each of which is also incorporated herein by reference. Still other suitable clustering mechanisms well known in the art include average-link, single link Ward's clustering, Nearest Neighbor, and K-means.

In general, SOM clustering may operate as follows. First, the computer may establish a k×k SOM grid of clusters. The choice of dimension, k, may be based on the number of molecules to be clustered as well as the desired separation between the molecules and is therefore a matter of design choice. A reasonable value of k in an exemplary embodiment is 20, thus providing 400 clusters. The computer may then randomly seed each cluster in the grid with connection weights defining a cluster template. Each of these weights is preferably a real value from 0 to 1. (The weights shown in FIG. 3 may be scaled by a factor of 100 to achieve these values.) Each cluster template is preferably a vector of a length corresponding to the total number of substructure keys used to describe the molecules, and each element of the template may correspond to one of the substructure keys. Thus, where there are preferably 157 substructure keys, each cluster template in an exemplary embodiment may be a 157 element vector.

The computer may then cycle through the descriptor vectors of the molecules at issue and places each vector into the SOM grid. The vector of the first molecule will fall into the cluster whose randomly seeded template is closest to the vector. In this regard, for instance, the computer may compute the Euclidean distances between the input descriptor vector (i.e., the vector being inserted into the grid) and each cluster template, and the computer may then assign the vector to the cluster with the shortest computed distance (representing a closest match). Each time a molecule falls into a cluster, the computer may then adjust the weights of that cluster to be closer to the weights defined by the inserted descriptor vector. For instance, if a vector defines a 1 for a particular substructure key, and the corresponding connection weight in the cluster into which the vector best fits defines a weight of 0.6 for that key, the computer may increase that connection weight in the cluster template.

The adjustment from a current cluster template connection weight to a new weight based on the weight of an input node (i.e., an input description vector) can take any form and, for example, may comprise a simple average. Alternatively, in an exemplary embodiment, the computer may adjust each connection weight in the cluster template to be a weighted average of its current weight and the input weight. In this regard, the weight change may be defined by the formula $W_{new}=W_{old}+\alpha(X_{input}-W_{old})$, where $W_{old}$ is the current (or old) connection weight defined by the cluster template, $X_{input}$ is the weight of the corresponding node of the input data, $\alpha$ is a weighting factor, and $W_{new}$ is the resulting new connection weight for the cluster template. In an exemplary embodiment, the computer may decrease a as the SOM training process proceeds, beginning at around 0.8 and progressing to a low value of 0.1. (When a is 0.5, a simple average results).

After adjusting the weights of the cluster in which the molecule fell, the computer preferably adjusts the weights of the clusters neighboring this cluster in the SOM grid. These weights are preferably adjusted to a lesser degree as the distance from the molecule's cluster increases. Thus, the more structurally similar the next molecule, the closer it will fall in the map to cluster. Ultimately, this achieves local organization or focal points in the grid, defining regions of molecules having similar features.

Each molecule is placed on the grid in this fashion, adjusting the weights of the cluster and neighboring clusters for each. Once all of the molecules have been placed on the grid, they are removed and the process is repeated, refining the connection weights learned in the first pass. By repeating the clustering process over many iterations (on the order of 100 s or 1000 s for instance), the SOM grid ultimately becomes stable, learning to associate cluster templates with molecules based on the importance (weights) of features to particular clusters in the grid.

Training of the SOM grid is preferably complete when every molecule in a current iteration falls in the same cluster as in the last iteration. After training is complete, the nodes of the SOM grid are defined by a weighted descriptor vector (template) with trained weights. The structural keys corresponding to each highly-weighted bit in a cluster's feature vector are then important dimensions of structural similarity for the molecules in the node. (In particular, if many molecules that fit within the cluster have a particular substructure key in common, the connection weight associated with the substructure key will approach a binary 1 or the weight of the particular key.)

SOM clustering does not necessarily establish what makes molecules active but rather what substructure features the molecules have in common. It is reasonable to assume initially, however, that this structural similarity may relate to a common activity characteristic represented by a given cluster, particularly when a high concentration of active molecules fall within the cluster. In other words, the computer may use the SOM clustering process to discover correlations between structure and activity.

V. Identifying Hot-Spots

In this stage, according to an exemplary embodiment, the computer evaluates the SAR per cluster and/or per neighborhood of clusters (metacluster) by considering the activity of the molecules in a given cluster or group of clusters. The object at this point is to identify areas or hot spots in the SOM grid that represent or exhibit a high concentration of activity (based on the activity level of the molecules in the area), which can reasonably be correlated with the structural similarity of the molecules in the identified area. Since training the SOM grid achieves localized organization of molecules based on their structural similarity, some areas of the grid may have a high concentration of active molecules and others may have low concentration. Some clusters may contain many active molecules, others may contain few active molecules, and still others may contain no active molecules at all. In identifying hot spots, the computer preferably looks for areas of high concentration of activity.

At this stage, the SOM map has already become stable, and its clusters are each represented by a template/vector indicating weights (or binary value) for each possible substructure key. It is no longer training. The computer may now evaluate structure-to-activity relationships, for example, by considering the activity levels of the molecules in each cluster. Thus, for example, the computer may cycle through the clusters in the SOM grid and determine how many active molecules are in each cluster and/or calculate the average activity level of the molecules in the cluster. In turn, if the number of active molecules or the average activity level of the molecules exceeds a predetermined threshold level, then the computer may select the cluster as a hot spot.

Further, the computer may extend this exemplary analysis to wider areas of the SOM grid. For instance, if a neighborhood of several adjacent clusters contains a relatively large number of active molecules compared to other areas, the computer may reasonably conclude that the structural similarity defined by the neighborhood is correlated with the high activity of the molecules in the neighborhood. Therefore, the computer may designate the neighborhood as a hot spot.

Since the phylogenetic tree is preferably trained with active molecules only, so too is each SOM grid trained with active molecules only. In that context, the computer may for example identify as a hot spot (or as the core of a hot spot) any cluster that contains at least two active molecules (hereafter a non-singleton cluster). Additionally, the computer may take into consideration the relative levels of activity, weighing more heavily higher levels of activity in determining whether an area in the grid should constitute a hot spot.

The computer may alternatively employ other criteria as desired to select one or more suitable hot spots that appear to correlate structure with activity. The goal at this point should be to increase the odds of learning a useful new substructure key in the next stage. Thus for example, and without limitation, the computer may rank a set of potential hot spots according to average activity level and may then select only a predetermined number or percentage of the potential hot spots that have highest average activity levels.

Figure 6:
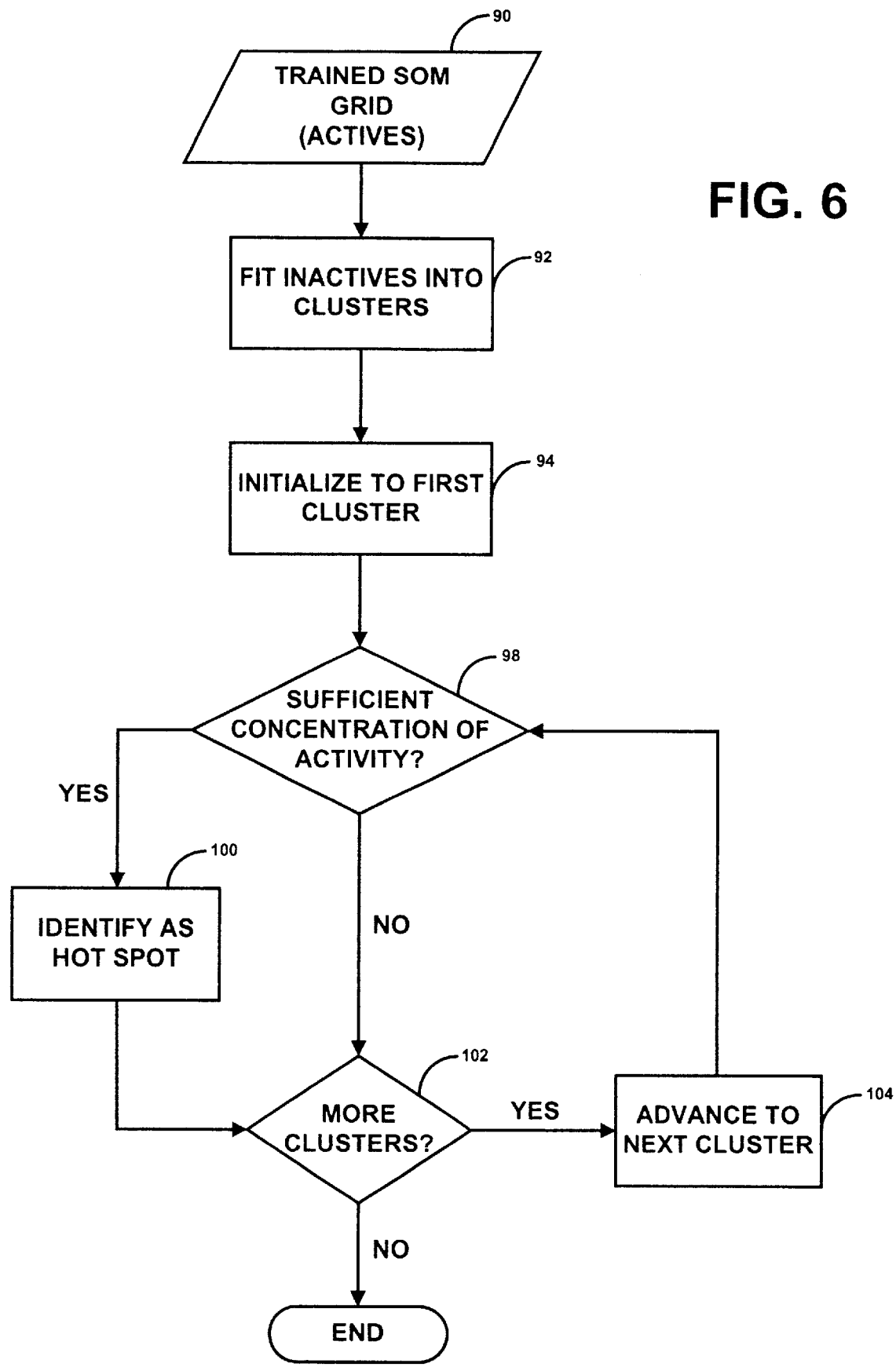
FIG. 6 is a flow chart depicting an exemplary set of functions that a computer may perform to identify hot spots according to an embodiment of the present invention.

Referring to the drawings, FIG. 6 illustrates a set of functional blocks that may be employed in identifying hot spots according to an exemplary embodiment. As shown in FIG. 6, at block 90, the computer begins with a trained SOM grid, which, in an exemplary embodiment, was trained with only active molecules. At block 92, the computer may fit each of the inactive molecules into the cluster of the SOM grid whose template the descriptor vector of the molecule most closely matches. At block 94, the computer may initialize a pointer to the first cluster, to facilitate cycling through the clusters.

At block 98, the computer may determine whether the cluster exhibits or represents a sufficient concentration of activity. This decision may involve determining whether the cluster contains more than J active molecules. J is preferably an adjustable parameter and is therefore a matter of design choice. The choice of a value for J may be based on the diversity of the molecules in the data set and the size of the SOM grid. For instance, J may be higher (e.g., 10) for highly similar sets of molecules being clustered, as in a very focussed screening data set, and J may be lower (e.g., 2) for larger, more diverse sets.

If the computer determines that the cluster represents a sufficient concentration of activity, then, at block 100, the computer may designate the cluster as a hot spot. In turn, at block 102, the computer may determine whether more clusters exist in the SOM grid. If so, then, at block 104, the computer may advance to the next cluster and return to block 98 to evaluate the structure-activity relationship of the cluster.

In an exemplary embodiment, each hot spot has a discriminating set of features that defines the similarity of molecules in the hot spot. As an example, where the hot spot is a single cluster, the discriminating set of features may be defined by the substructure keys of the cluster template, to which the molecules in the cluster most closely match. As another example, where the hot spot is a neighborhood of clusters, the discriminating set of features may be defined by some function of the cluster templates of the various clusters in the neighborhood. For instance, the discriminating set of features may be an average of the cluster templates or the union of the cluster templates or some other function.

Further, the discriminating set of features may for example exclude any substructure keys that are not present in the hot spot (for instance, any substructure keys that have a binary 0 value in the cluster template for a cluster defining the hot spot) or that have less than some threshold weight or relative weight. The computer may reasonably conclude that such substructure keys are not responsible for structural similarity of the molecules in the hot spot and therefore do not distinguish or define the hot spot.

It should be appreciated that hot spots could be selected in a different fashion if a different grouping mechanism (i.e., other than SOM clustering) were used. For instance, the molecules in the node could be clustered using Wards clustering, and, of the clusters thereby established (and/or metaclusters of those clusters), those having the highest or other desired activity levels may be selected as hot spots. Alternatively, as noted above, the decision could be based simply on the number or density of molecules in the potential hot spot.

vi. Learning New Substructure Keys

In an exemplary embodiment, once the computer has selected one or more hot spots, the computer may actively map the discriminating features of each hot spot back to the molecules in the hot spot so as to discover what the clustering learned. That is, the computer may discover the most significant structural similarity (or similarities) in each hot spot. This significant structural similarity may be deemed to be at least a potential new learned key.

The idea here is to build a composite structure of components (e.g., atoms, bonds and/or other features) that best represents the structural similarities of the molecules in a hot spot and that, therefore, most likely correlates with the observed activity of the molecules. In an exemplary embodiment, this composite structure is not just the similar substructure keys in the molecules of a given hot spot. Rather, because the exemplary embodiment is particularly interested in chemical reactions, the process of learning the composite structure may preferably take into consideration where in the molecules the substructure keys fired or, in other words, what components of the molecules caused the substructure keys to fire.

For instance, several molecules in a hot spot may have several keys in their descriptor vectors in common, but these keys might not be set by the same substructure in all the molecules. In that case, the computer may reasonably conclude that there is no composite structure of interest in all of the molecules. However, if the computer determines that a significant set of keys common to all the molecules in the hot spot are set by matching a larger composite substructure that appears in a relatively large number of molecules in the hot spot, then the computer may reasonably conclude that the composite structure is of particular interest.

The result of clustering with descriptor vectors that are based on MACCS-like keys (e.g., SMARTS strings) is clusters of molecules with somewhat similar structures. However, the MACCS-like keys are unable to differentiate between structurally dissimilar molecules that set the same keys in the descriptor vector. This happens quite often because the keys are "redundant," describing small substructures of the molecule with multiple keys. A more representative feature of the molecules is the maximum common substructure (MCS) that is contained in all of the molecules in a hot spot (i.e., the largest contiguous (or, alternatively, non-contiguous) subgraph common to all the molecules (graphs)). The MCS or other common substructure identified at this stage of the process can be a 2D or 3D arrangement. Thus the common substructure can, for instance, be a 3D arrangement of chemical features.

Therefore, in accordance with an exemplary embodiment, a computer should seek to find the MCS among the molecules within each hot spot. If the computer finds a most common composite structural component in a hot spot, the computer may reasonably conclude that the structure is correlated with (or responsible for) the structural categorization of the molecules. Therefore, the computer may select the MCS (or some fraction of the MCS) as a new key. In addition or alternatively, the computer may derive new keys from other common substructures (non-MCS) in the molecules that define the hot spot.

The computer may identify the MCS among a set of molecules in any desired fashion, including, without limitation, by applying a genetic algorithm, by applying an exhaustive search for all common substructures and selecting the largest of the identified substructures, or by comparing graphs of the molecules. In an exemplary embodiment, the computer may identify an MCS among a set of molecules by employing subgraph isomorphism, which is a technique well known to those skilled in the art.

A goal of the exemplary embodiment, however, is to generate pharmacophorically "interesting" or "useful" structural information. Therefore, instead of searching for merely the maximum common substructure among the molecules, the computer may beneficially look for the maximum pharmacophorically important common substructure (i.e., a pharmacophorically important MCS) among the molecules. To accomplish this, as presently contemplated, the computer may take advantage of the redundancy inherent in the keys, using the redundancy as a way to identify what parts of the molecules in the hot spot define the similarity in the key dimensions.

As noted above, each of the substructure keys employed by the computer (e.g., received as input data) may be weighted. Alternatively, each key may be assigned a binary weight of 1, such that all keys have the same weight. According to an exemplary embodiment, the computer may weigh the atoms (and/or bonds and/or other features) in the molecules of the hot spot with the sum of the weights of every key whose "hit" involves that atom. In this way, the computer can see the relative "importance" of each atom to the similarity that defines each hot spot and use this information to drive the discovery of the pharmacophorically important MCS.

Figure 7:
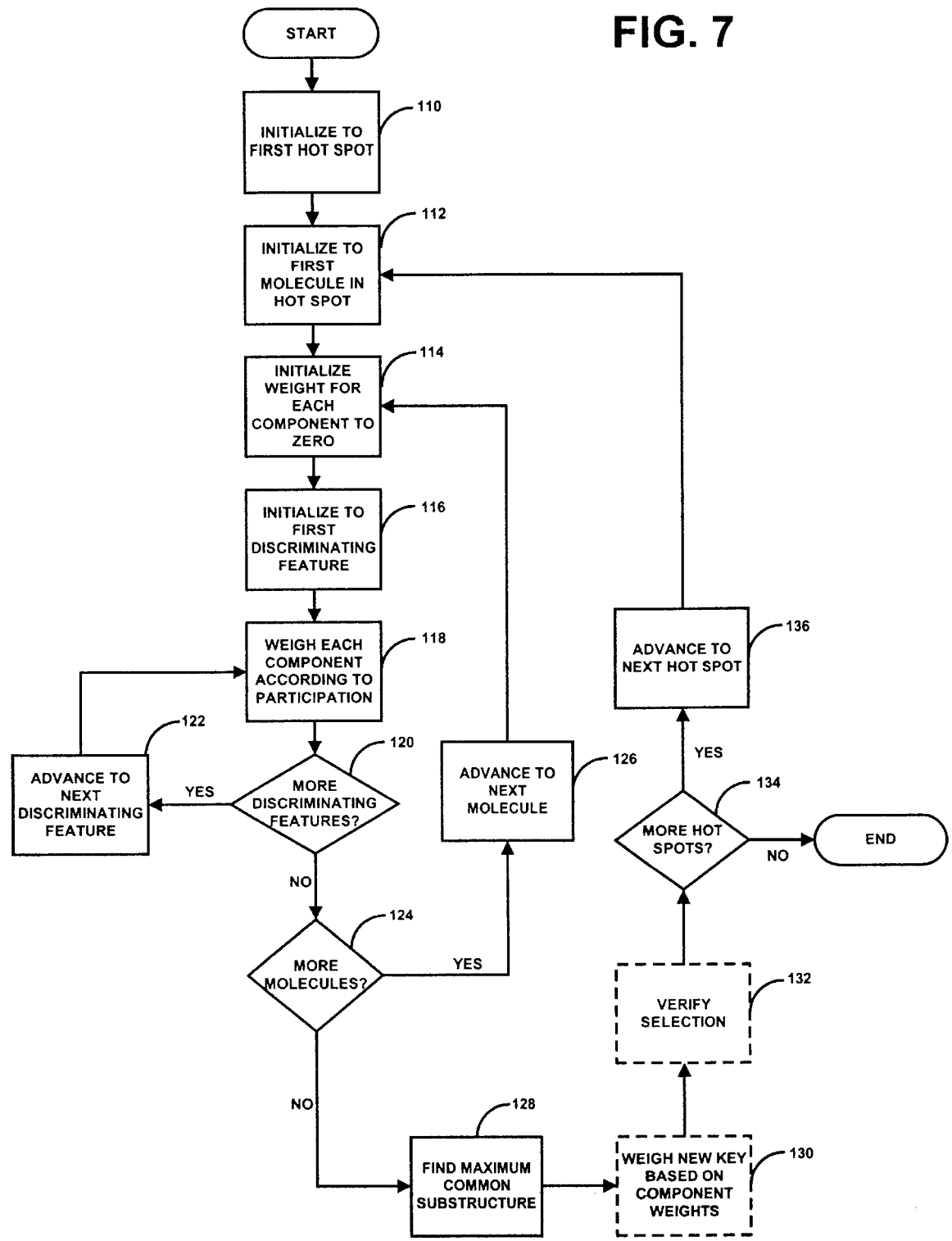
FIG. 7 is a flow chart illustrating an exemplary set of functions that a computer may perform to learn one or more new keys according to an embodiment of the present invention.

FIG. 7 depicts an illustrative set of functional blocks that may be involved in learning new keys according to this aspect of an exemplary embodiment. Referring to FIG. 7, at block 110, the computer may first initialize a pointer to the first hot spot. For the given hot spot, at block 112, the computer may further initialize a pointer to the first molecule in the hot spot. At block 114, the computer may then establish a weight for each component in the molecule and initialize the weight to zero. In an exemplary embodiment, the computer considers and weighs only atoms (although the computer could consider other components or aspects of the molecules as well). At block 116, the computer may then initialize a pointer to the first of the substructure keys or other indicia that defines the discriminating features of the hot spot.

At block 118, the computer may then weigh or "score" the atoms within each of the molecules in the hot spot by the number of times that they participate in matching the substructure key. In this regard, the computer may look for "hits" or instances where a substructure key appears in the molecule. For each such hit, the computer may add the weight of the substructure key to the weight of each of the atom(s) that the key hit. Thus, for instance, if the substructure key C—N has a weight of 0.7 and the key hits in a given molecule, the computer may add the weight 0.7 to the weight of the subject carbon atom and nitrogen atom in the −20 molecule. Alternatively, for instance, if the C—N key has a binary weight of 1, then the computer may increment the weights of each of the two atoms by a value of 1. This increase in weights thus reflects participation of those atoms in defining the structural similarity of the molecules in the hot spot.

At block 120, the computer may next determine whether additional discriminating features exist for the hot spot. If so, then, at block 122, the computer may increment to the next discriminating feature and return to block 118. If not, then, at block 124, the computer may determine whether additional molecules exist in the hot spot. If so, then, at block 126, the computer may increment to the next molecule and return to block 114.

In an exemplary embodiment, at block 128, once the computer has scored the participating atoms of the molecules in the hot spot, the computer may analyze the molecules in an effort to identify and select a maximum common substructure of all of the molecules in the hot spot. The computer may employ any suitable method to identify maximum common substructures. By way of example and without limitation, the computer may employ a genetic algorithm to compare the molecules and to identify a largest common substructure.

In an exemplary embodiment, the maximum common substructure (MCS) should be a contiguous common substructure among the molecules in the hot spot. However, the common substructure may alternatively be a non-contiguous structure. Further, in addition to or instead of finding the maximum common substructure, the computer may seek to find any common substructure(s) among the molecules (i.e., whether or not contiguous). The computer may deem the common substructure (and preferably the MCS) to be a reason for the structural similarity of the molecules that define the hot spot. Therefore, the computer may select each such common substructure as a new key and/or pharmacophore.

Further, although the preferred embodiment contemplates identifying only one, maximum common substructure in each hot spot, the computer can alternatively be arranged to identify more than one of the common substructures in the hot spot. By considering common substructures in addition to (or instead of) the MCS, the computer can effectively identify more pharmacophoric mechanisms.

In an exemplary embodiment, the computer may render its comparison of molecules more efficient by first deleting from a stored representation of each molecule any atom that has scored less than a threshold value (such as the median weight of all atoms in the molecule for instance). The computer then preferably applies a genetic algorithm to find at least the MCS of the remaining molecular structures. An example of a suitable genetic algorithm is a modified version of that described in "Matching Two-Dimensional Chemical Graphs Using Genetic Algorithms," Robert D. Brown, Gareth Jones, and Peter Willett, J. Chem. Inf. Comput. Sci., 1994, 34, 63–70. The entirety of the Brown et al. reference is hereby incorporated by reference. The Brown reference describes how to use a genetic algorithm to generate the maximum common substructures between two molecules. As presently envisioned, by way of example, the Brown algorithm can be modified in several respects.

First, the Brown algorithm may be modified to establish the maximum common substructure between possibly more than two molecules (as a hot spot may contain more than two molecules). In this regard, when the computer compares two molecules, the computer may maintain a record of all potentially matching substructures (rather than identifying only the maximum common substructure). The computer may then use these potentially matching substructures when comparing the match between the two molecules to a third molecule. For example, the computer may generate all potential common substructures when comparing the first two molecules and then restrict its comparison to the third molecule to these potential common substructures. The computer may continue this procedure until it has completely analyzed all of the molecules. Once all of the molecules in a group have been analyzed, the computer may then conclude that the largest common substructure remaining is the maximum common substructure of this group of molecules.

Second, the computer may assign weights to atoms of the individual molecules and use these weights in the fitness function of the genetic algorithm. For example, assume that four given keys such as MACCS keys all hit an atom A1 in the first molecule and also all hit an atom A2 in a second molecule. Assume further that another atom A3 in the second molecule is hit twice by only two of the four keys. Therefore, the difference between the weights of atoms A1 and A2 is less than the difference between the weights of atoms A1 and A3. In this example, T5 based on the atom weights, the fitness function may consider atoms A1 and A2 to be a better match than atoms A1 and A3. Thus, the computer may update the fitness value to reflect the match between A1 and A2. In this way, the keysets used to differentiate the molecules can be used to guide/bias the genetic algorithm's procedure for choosing which two atoms should be matched when there are a number of potential matches, thereby allowing it to potentially converge faster.

Still further, the computer may use the weights to reduce the number of matches that need to be searched in the genetic algorithm to determine a set of atom matches between two molecules. For instance, in the preceding example, the computer may consider atoms A1 and A2 to be a potential match, while the computer may determine that atoms A1 and A3 are above a weight difference threshold and therefore are not a valid match. Because of the threshold, the number of potential matches to be considered in finding the MCS is reduced. Reducing the search space for the genetic algorithm in this way allows it to potentially converge more quickly.

In the exemplary embodiment, an illustrative fitness function for comparing two molecules may operate as follows. First, the computer may define the maximum allowable difference (MAD) to be 20% of the weight on an atom. Second, the computer may define DIFF to be the absolute value of the difference between the weight on an atom in one molecule and the weight on an atom in the other molecule. In turn, the computer may determine whether DIFF is greater than MAD. If so, then the computer may conclude that the atoms do not match. If not, the computer may adjust the fitness value via the following formula:

$$\text{New fitness} = \text{Old fitness} + 10.0 * (\text{MAD} - \text{DIFF})/\text{MAD}.$$

Of course, the foregoing provides only an example of a genetic algorithm for use in identifying maximum common substructures. Suitable variations and/or other algorithms may exist as well.

In the exemplary embodiment, the original set of 157 keys remains constant throughout the generation of the phylogenetic-like tree. However, in an alternative embodiment, as described in co-pending application Ser. No. 08/281,990, each newly learned key can be added to the original set of keys to increase the descriptor set available for subsequent analysis. If that is done, then the computer should preferably assign a weight to each newly learned key, so as to establish the relative importance of the new keys in describing two molecules as similar. FIG. 7 illustrates this function at block 130.

In particular, at block 130, the computer may weight each new substructure key based on the weights of its components. As an example, without limitation, the computer may set the weight of the new substructure key equal to the average weight of the atoms (or other components) that make up the learned key. For instance, the computer may set the weight of the new substructure key equal to the average weight of the atoms (or other components) that make up the substructure matched by the learned key in each of the molecules in the cluster (or other hot spot). In this example, the computer may take the average over all the atoms in all of the matching substructures in all of the molecules. Alternatively, for instance, the computer may select one molecule (or a subset of molecules) in which the learned key hits (with no particular preference to which molecule, for instance), and the computer may take the average of the atoms in that matching substructure.

In addition, as shown at block 132, the computer may also seek to verify the accuracy, or usefulness, of each new learned key. To do so, for instance, the computer may determine whether the new key defines a neighborhood of clusters, that is, whether the same key exists in neighboring clusters of the SOM grid. By way of example, for each cluster neighboring the cluster under analysis, the computer can run a SMARTS query against each of the SMILES strings representing the molecules in the cluster. If the computer finds at least some defined number of matches (e.g., 2), then the computer can conclude that the new key is pharmacophorically useful. Otherwise, the computer can conclude that the new key does not define an interesting (e.g., commercially valuable) structure-to-activity relationship and the computer may therefore opt to reject the new key.

As another example, the computer may apply a rule that a newly learned key is useful only if it originates from a cluster or other hot spot of at least some defined number of compounds. For instance, if the hot spot includes less than 3 compounds, the computer may opt to reject the key (or not establish a key from that hot spot in the first place).

The minimum number of hits in neighboring clusters and the minimum number of molecules in the core cluster of the hot spot (as well as any other such heuristics) can be user-specified parameters, which may depend on the problem being solved. For highly similar sets of molecules being clustered, as in a very focussed training set, the requirements may be very loose, such as 2 or more molecules and a hit in at least 0 of the neighboring clusters. For larger more diverse sets, more coarse criteria may be desirable, such as learning in only clusters of 10 or more molecules and requiring that the key hit in 4 or more molecules from neighboring clusters. Thus, the functions performed may depend on whether the computer is seeking to learn coarse or fine-grained discriminations between sets of active molecules, for instance.

In turn, at block 134, the computer may determine whether more hot spots exist in the SOM grid. If so, then, at block 136, the computer may advance to the next hot spot and return to block 112. If not, then the computer may conclude that it has finished identifying potential new keys.

The number of new keys learned at this stage may vary. While, in an exemplary embodiment, the upper limit is one new key learned per cluster in the SOM grid. In that case, the maximum number of new keys learned from a given node of the tree may depend on the size of the SOM grid. In practice, however, no more than 10% to 30% of the clusters in the grid will result in newly learned keys.

vii. Applying the New Keys as Filters to Grow Children Nodes

Once the computer has learned new keys that define what may be pharmacophorically important feature sets, the computer next applies these new keys as filters to grow children nodes in the tree. The idea at this point is to perform a multi-domain sub-classification of the molecules of the node. All of the molecules that include the feature set defined by the new key will pass into a child node that corresponds to that new key.

Thus, for example, assume that there are 1000 active molecules in the root node 0 and three learned keys A1, B1 and C1 are selected from hot spots in the SOM grid trained on these molecules. It is hypothetically possible that 700 of the molecules may fire on learned key A1, to therefore produce a child node 1 that contains the 700 molecules; 450 of the molecules may fire on learned key B1, to therefore produce a child node 2 that contains the 450 molecules; and 800 of the molecules may fire on learned key C1, to therefore produce a child node 3 that contains the 800 molecules. There may thus be some overlap between the molecule sets in the sibling nodes, since the molecules of the parent are not split by rote into mutually exclusive classes.

The computer may generate the same number of children nodes as there are keys that it learned from the parent node. Alternatively, however, the computer may determine that one or more of the newly learned keys should not be applied. For instance, it is possible that two of more of the keys learned from a given node may be identical. In that case, it would make little sense to grow two identical children nodes (siblings). Therefore, the computer may be programmed to grow a child node based upon only one instance of such duplicates. As another example, it is possible that one of the learned keys may be a subset of the parent key (to the extent a key was used to define the parent—i.e. if the parent is other than the root node). In that case, since all of the molecules in the parent would also include the new key, the computer may be programmed to not grow a child from that new key.

As still another example, it is possible that one of the learned keys may be a superset of another learned key. In order to achieve finer granularity of information in the tree structure, the computer may be programmed in that situation to grow a child node based upon only the smaller, i.e., simpler, key (according to a principle of parsimony). For instance, if one new key is C—C—N and another new key is C—C—C—N, the computer may select the C—C—N. A rationale for this function is that the larger key is likely to result later in the tree, and, by selecting the smallest key, it is possible to create a more detailed tree structure, with smaller steps as each filter point. For instance, by selecting C—C—N as a filter, the next level of the tree structure may show that some molecules have C—C—C—N as a common key and others have N—C—C—N as a common key, whereas the pharmacophore N—C—C—N may not have resulted from the current node.

Figure 8:
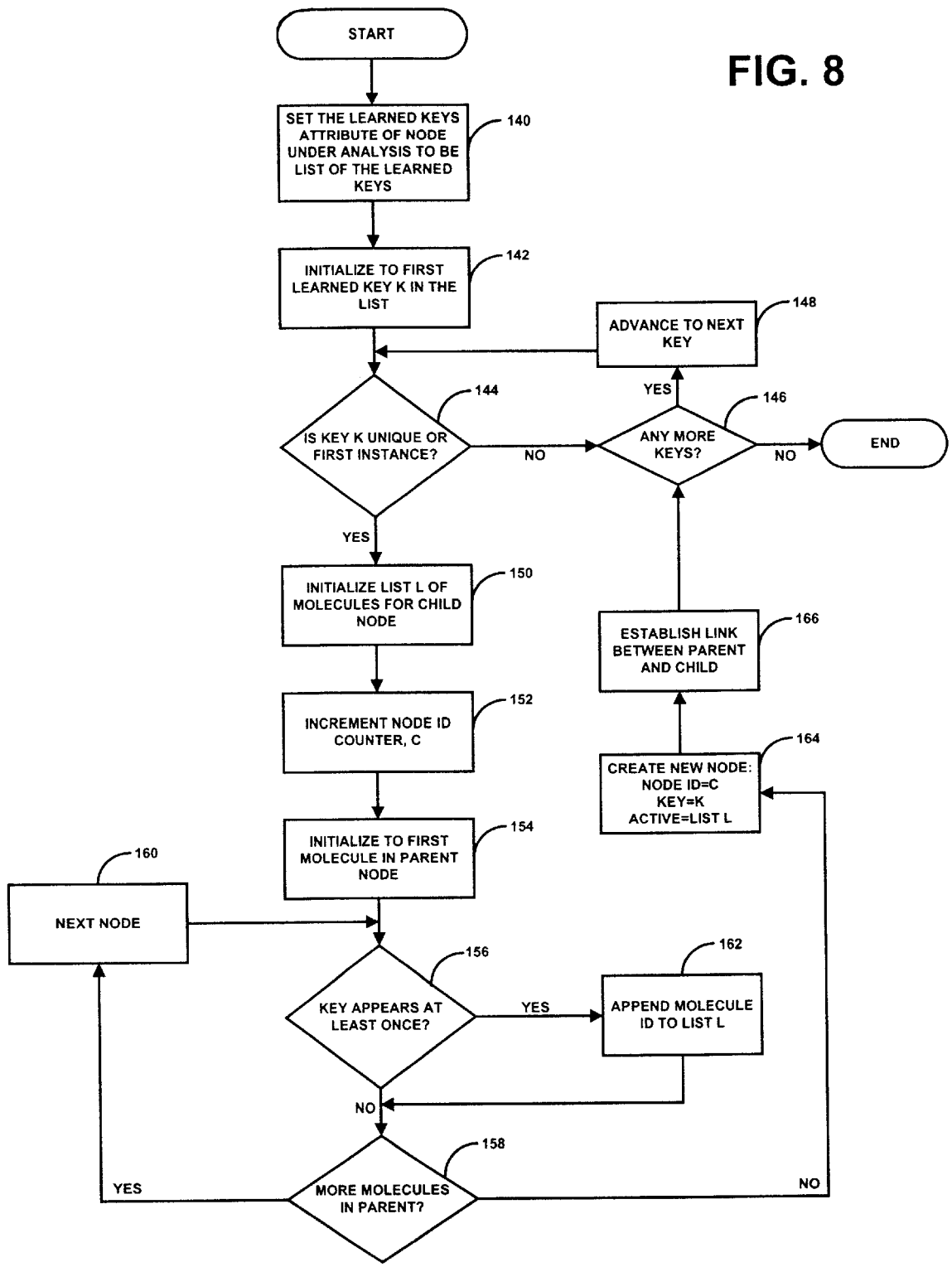
FIG. 8 is a flow chart illustrating a set of functions that a computer may perform to apply newly learned keys as filters for growing child nodes in an embodiment of the present invention.

FIG. 8 depicts an illustrative set of functional blocks that may be involved in growing children nodes based on the newly learned keys. As shown in FIG. 8, at block 140, the computer sets the "learned keys" attribute of the current (parent) node to be a list of the keys that the computer learned from this node. Alternatively, it is possible that the computer may generate that attribute list as it learns the new keys, i.e., during the process illustrated in FIG. 7. At block 142, the computer initializes a pointer to the first learned key, k, in the learned keys list.

At block 144, the computer next determines whether key k is a unique key in the list of keys generated from the parent node or, if not, whether it is the first instance of the key. (The latter criterion of course subsumes the former and may therefore be the sole test at this point). If not, then, at block 146, the computer determines whether any additional keys exist in the list. If so, then, at block 148, the computer advances the pointer to the next key in the list and returns to block 144. If no further keys exist in the list, then the computer may conclude that it has finished growing children nodes from the newly learned keys.

If the key, k, is the first instance of a key established from the parent node, at block 150, the computer initializes a list, L, of molecules that will be represented by a child node and, at block 152, the computer increments its node counter, c. At block 154, the computer initializes a pointer to the first molecule in the parent node, i.e., the first molecule in the "actives" attribute list of the parent node. At block 156, the computer then determines whether key k appears at least once in the molecule. To do so, as above, the computer may query a SMARTS representation of the new key against the SMILES representation of the molecule. If the computer finds no hits in the molecule, then, at block 158, the computer determines if additional molecules exist in the parent node. If so, then, at block 160, the computer advances the pointer to the next molecule in the parent and returns to block 156.

If the computer determines that key k appears at least once in a molecule of the parent node, then, at block 162, the computer appends the molecule to the list L of molecules to be represented by the child node. The computer then returns to block 158 to determine whether any additional molecules exist in the parent node.

Once the computer has finished applying key k as a filter to all of the molecules in the parent node, at block 164, the computer creates a new child node. (Alternatively, the computer could create the new node as it proceeds). For the child node, the computer may assign the counter value c as the "node ID" attribute, the key k as the "key" attribute, and the list L as the "actives" list attribute. In turn, at block 166, the computer may link the child node to the parent node, for instance, by establishing an appropriate pointer. (In this regard, each node of the tree may include a "pointer-up" attribute and a "pointer-down" attribute, to establish links between parents and children). The computer may then proceed to block 146, to determine whether any more keys exist on which to filter the molecules of the parent node, and so forth as described above.

After filtering on the keys learned from a given parent node, the computer may set the "status" attribute of the parent node to "clustered," to indicate that the node has been successfully analyzed.

viii. Selecting Nodes to Explore Further/Growing the Tree

Once the computer has finished filtering the molecules of a given parent node to grow new children nodes, the computer may then decide which node of the tree to next explore further. In this process, the computer may effectively rank or rate the "leaf" nodes of the tree (i.e., the nodes that have no children) to determine (i) whether the nodes should be explored further and (ii) in what order the nodes should be explored.

In this regard, the tree growing preferably stops when all the subsets of active molecules have been sufficiently accounted for along all available branches or paths. When generating the tree, the computer may encounter a lot of redundancy in new keys that arise and subsets of molecules that are formed as the tree grows. In the currently preferred embodiment, branches of the tree are pruned when this redundancy appears, as there is no need to follow a branch from a parent node that has already been explored (such as where the same branch has already been developed elsewhere in the tree, for instance).

There may be several reasons that the computer may decide to not explore a leaf node further, i.e., to prune a branch of the tree. The following are several examples of such reasons:

1. Insufficient data. If the number of molecules contained in the node is less than some defined number (e.g., a user-specified parameter, on the order of 10, 15 or 20 for instance). In that case, it is reasonable to conclude that the node is too small to result in sufficiently useful information.

2. No change in molecule set. If the set of molecules in the node is the same as the set of molecules in its parent node. In that case, it is reasonable to conclude that no further useful information can be gleaned from exploring the node.

3. Key is improper subset of parent key. If the learned key that gave rise (as a filter) to the node is a subset of, or identical to, the learned key that gave rise to its parent. In that case, it is reasonable to conclude that further information gleaned from the node will be no better than the information gleaned from its parent, since the learned key is less discriminating than its parent key.

4. Molecule set is identical to another node. If the set of molecules in the node is the same (or almost the same, within some small percent) as the set of molecules in any other node in the tree. In that case, it is reasonable to conclude that no further useful information can be gleaned from exploring the node.

In the exemplary embodiment, the computer may be programmed to cycle through each of the nodes in the tree that does not already have an assigned "status" attribute and to determine whether such nodes satisfy any of the above or other desired tests. If the computer determines that a node satisfies one of these tests, the computer may record an appropriate indication as the node's status attribute. The indication may signal to the computer that the computer should not explore the node further. Alternatively, the indication may signal to the computer that the computer might not explore the node further. As an example of the latter instance, if the computer determines that the "actives" attribute of a given leaf node is identical to that of another leaf node, the computer may mark both as duplicates of each other (noting the node ID of the duplicate for reference in each). But the choice of which duplicate to pursue may depend on other criteria such as the desired order of growing the tree.

In the exemplary embodiment, the computer may label each leaf node that it determines should not be explored further as a "stop node" (a status attribute). Depending on design choice, the computer may be programmed to prune a branch of the tree below the stop node (i.e., retaining the node in the tree structure) or above the stop node (i.e., deleting the node from the tree structure). A benefit to leaving the a node in the tree is to establish yet additional useful pharmacophoric information for use by a chemist.

In contrast, the computer may label each leaf node that it determines should possibly be explored further as a "go node." In turn, the computer may then determine which of the go nodes to explore next. The object in this process is to determine how the computer can more efficiently or completely generate commercially valuable information about pharmacophoric growth.

In an exemplary embodiment, the computer generates the tree structure in a "depth-first" (DFS) manner, meaning that the computer seeks to generate an entire branch until it is pruned, before returning to generate subclasses from the closest ancestor node. Alternatively, the computer can be configured to generate the tree in a "breadth-first" (BFS) manner, by which the system explores all nodes of a given level (i.e., generation) of the tree before proceeding to the next level of the tree. The breadth-first technique results in a shallower, broader tree compared to the depth first technique. Still alternatively, the computer can generate the tree in a "diversity first" (DivFS) manner, according to which the computer first explores the go node that contains the most structurally diverse set of molecules (as determined by taking an average of Tanimoto distance between all pairs of molecules in the node, for instance).

In addition, within the chosen growth method, the computer can preferably be programmed to explore the nodes in an order that is based on the size of the learned keys of the nodes. In particular, the computer preferably explores node with a smaller learned keys first.

By expanding the tree from the smallest new keys first, the computer forces the tree to be deeper, defining more levels or generations of useful pharmocophoric-growth information. More particularly, by starting with small keys that are present in a large number of molecules, the multi-domain classification of the molecules is less severe at early levels, since many molecules match the small keys. In turn, the subsets at the early levels are large, which leaves a greater possibility to discovery additional similarities of interest in subsequent branchings. The larger keys will be likely to arise again as the computer grows branches from the smaller keys, which is the currently preferred embodiment. In other words, the preferred embodiment allows larger keys to have a chance to be discovered under one of the branches formed from the smaller keys. In contrast, if the computer follows the larger keys (which is not excluded, but is not preferred), the tree will grow more shallow, which may in some circumstances be useful as well but is not currently preferred.

Similarly, if the computer encounters a node that has been labeled as a duplicate of another node in the tree (i.e., having the same set of molecules as the other node), but one of the duplicates has a smaller learned-key than the other, the computer may be programmed to explore only the node with the smaller learned key. This may be technique can be applied between sibling nodes or can extend more broadly to be applied between any two nodes if desired. For instance, of 500 molecules, if 215 pass through an N—N filter and the same 215 pass through a C—C—N filter, the computer has no need to continue along both branches. By continuing along the branch defined by the smaller key, the larger key will presumably (likely) result later in the lineage from that branch, since all of the molecules in the branch have the larger key in common as well.

In prioritizing new keys by size (in the exemplary embodiment), the computer may, for instance, count the number of atoms and/or other features in the learned keys. A node having a learned key with fewer atoms than another key could be given higher priority. Two nodes having learned keys with the same number of atoms could be ranked equally (and used in arbitrary order for subsequent analysis).

Figure 9A:
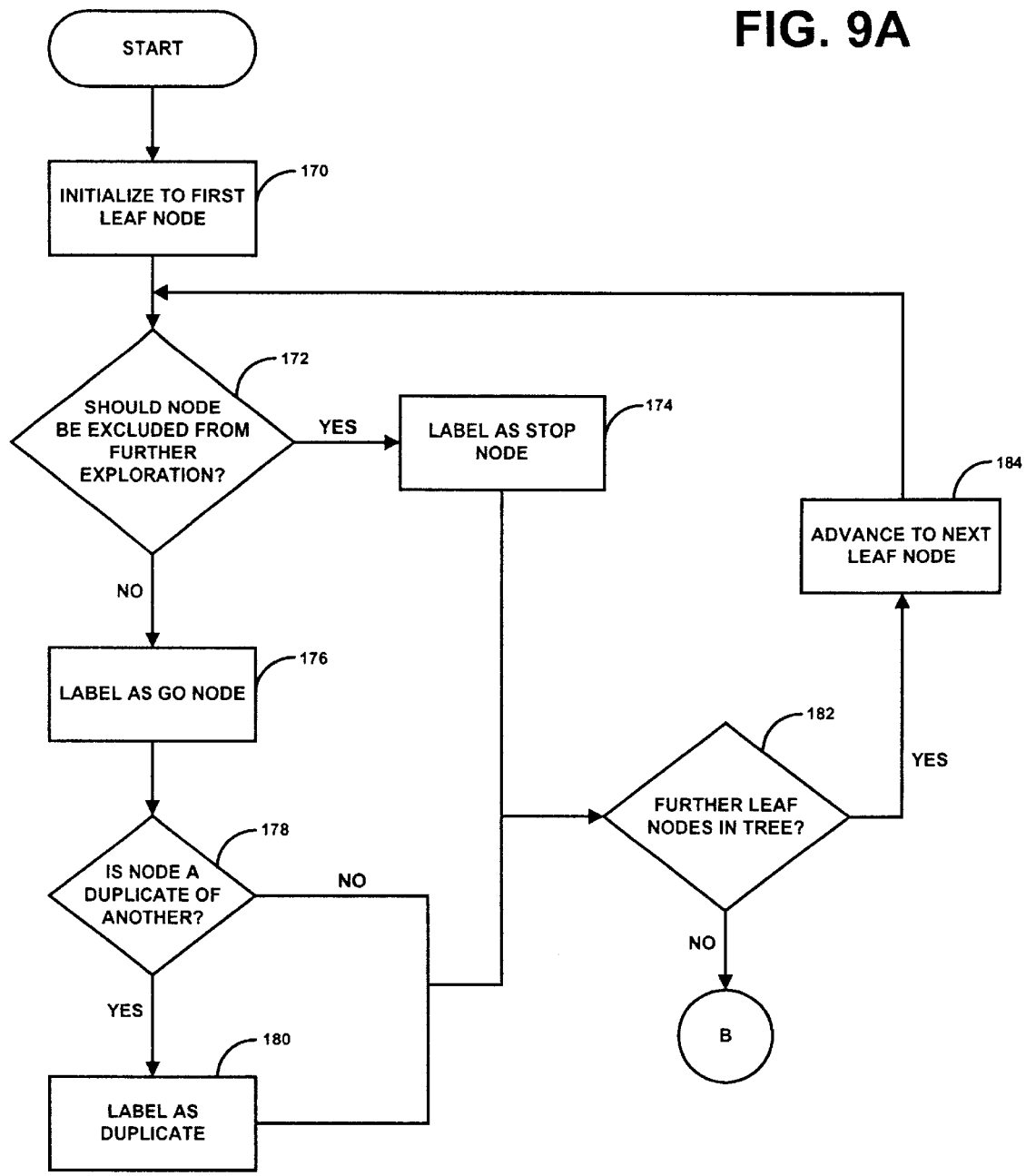
FIG. 9 (two parts) is a flow chart depicting an exemplary set of functions that a computer may perform to select a next node to explore in an embodiment of the present invention.
Figure 9B:
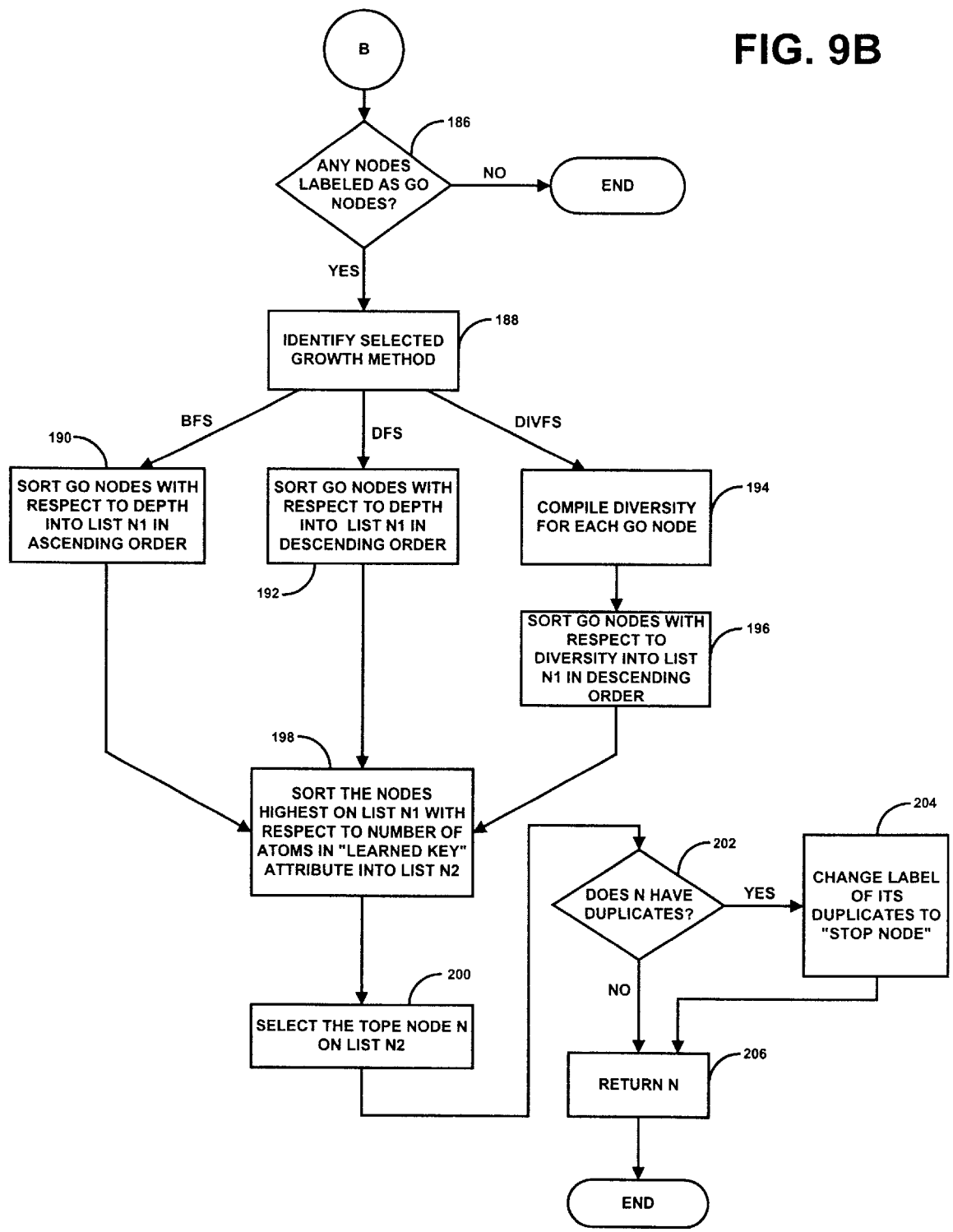

FIG. 9 presents an illustrative set of functional blocks that may be involved with growing the tree in an exemplary embodiment. As shown in FIG. 9, at block 170, the computer first initializes a pointer to the first leaf node in the tree (in any desired order). At block 172, the computer determines whether or not the node should be explored. In this regard, the computer may apply some or all of the tests described above and/or other tests. If the computer concludes that the node should not be explored, at block 174, the computer labels the node as a "stop node." If, on the other hand, the computer concludes that the node should possibly be explored, at block 176, the computer labels the node as a "go node."

At block 178, the computer also determines whether the leaf node is a duplicate of another node in the tree, in the sense that both nodes have the same set of molecules. If so, at block 180, the computer labels both nodes as duplicates of each other.

At block 182, the computer then determines whether additional leaf nodes exist in the tree. If additional leaf nodes exist, then, at block 184, he computer advances the pointer to the next leaf node and returns to block 172. Otherwise, the computer proceeds to block 186. There, the computer determines whether any leaf nodes in the tree are labeled as go nodes. If none are labeled as go nodes, the computer concludes that it has finished generating the tree.

If any of the leaf nodes in the tree are labeled as go nodes, then, the computer next proceeds to determine which go node to explore. For this purpose, at block 188, the computer may determine which growth method to use. As noted above, exemplary growth methods include BFS, DFS and DivFS. The computer can be programmed to employ only one of these methods. But in the exemplary embodiment, the computer will be programmed to receive user input selecting a desired growth method and to grow the tree according to that method.

If the selected growth method is BFS, then, at block 190, the computer preferably sorts the go nodes with respect to their depth (i.e., their level or generation from the root node) into a list N1 in ascending order. If the selected growth method is DFS, then, at block 192, the computer preferably sorts the nodes with respect to their depth into a list N1 in descending order. If the selected growth method is DivFS, then, at block 194, the computer evaluates the diversity of each go node (e.g., as an average Tanimoto distance between molecules in the node) and, at block 196, sorts the go nodes with respect to their diversity into a list N1 in descending order.

At block 198, the computer then sorts the nodes highest on list N1 by size of learned key into a list N2 in ascending order. For instance, if five members of list N1 are all tied for the top position on the list, the computer may compare the number of atoms in the learned keys of the five nodes and sort the five nodes from smallest (least number of atoms) to largest. At block 200, the computer then selects the top node N on list N2 as the node to explore next.

At block 202, the computer determines whether the selected node N has any duplicates, which would be indicated as described above. If node N has any duplicates, then the computer may be programmed to prevent further exploration of its duplicates. Therefore, at block 204, the computer may change the label on the duplicate(s) of node N to be "stop node." At block 206, the computer then concludes that node N will be explored next.

ix. Iterating

Having identified the node N to explore next, the computer then recursively repeats the above process. In particular, as described above, the computer groups the molecules of node N, identifies hot spots among the groups, learns new keys, filters the molecules on the new keys to grow children nodes, and selects a leaf node to explore next. The computer repeats this process until it reaches a conclusion (at block 186 in FIG. 9, for instance) that the tree has been fully explored. At that point, the computer has gleaned a substantial amount of commercially useful pharmacophoric information from the input data set, some or all of which it may output for viewing, analysis and use by a chemist, technician or other entity.

x. Outputting Results

According to the exemplary embodiment, the computer may provide an output indicative of its findings. A multi-domain tree grown in the manner described above will advantageously define a number of structural families representing pharmacophoric subclasses. The information defined by the tree can be very useful to a chemist, as it can, for instance, assist in the discovery of beneficial new pharmaceuticals.

The computer preferably stores for output a variety of information concerning each node of the tree structure. This information can include, for example, (i) the SOM map (or other indicia of structure-to-activity relationship) that the computer generated based on the molecules in the node, (ii) connection weights (template vectors) for the clusters in the SOM grid (which is very useful information if a need arises to recreate the tree, since SOM processing can be laborious and time consuming for the computer system), (iii) the learned key that defines common structure of the molecules in the node (for nodes other than the root node), (iv) all of the molecules that pass match the learned key and define the group of molecules in the node, and (iv) pointers to the parent node and the children nodes.

The output may take any suitable form for conveying some or all of the useful information generated by the computer. By way of example, the output may take the form of a tree structure stored in a computer memory, where each node in the tree can have parents and children. In this regard, the output can be provided to a chemist in the form of a relational database file, where a table of the database may define as records the nodes of the tree structure. Each record may include fields indicative of attributes of the node such as those described above and may include a parent field and child field, indicating which records are the node's parent (if any) and child (if any).

As another example, a description of the tree can be provided as a file structure stored on diskette or other computer storage medium. Examples of such file structures are well known in the art, and typically include readily accessible directories and subdirectories, each of which may include assorted files, properties and other information. Such file structures are particularly well suited to represent a tree of pharmacophoric-growth information generated in the manner described above. In particular, for instance, each directory can represent a single node of the tree, its subdirectories can represent its children nodes (if any), and its parent directory can represent its parent node (if any). One or more files or properties for the directory may include attribute information for the node as described above. For instance, each of the molecules (or its associated ID) may be contained within a respective file in the node's directory. Still further, each of the files or other portions of a directory can be arranged as a link (such as a shortcut or hyperlink) to other information such as images, graphs and descriptions of the molecules and keys associated with the node.

In an exemplary embodiment, a molecule viewer may also be provided, to allow a chemist or other person to view a 2D (or perhaps 3D) representation of a selected molecule in any given node. In addition, the whole tree structure can be displayed as a tree structure with an appropriate viewer.

A tree-viewer may be embodied as a software program executed by a computer processor, either integrally together with the pyramid-building system or as a separate module. In an exemplary embodiment, the tree-viewer streamlines the presentation of a tree structure to a chemist, by allowing the chemist to ask questions about the properties of individual tree nodes (clusters) and about the relationship between nodes, and by presenting the requested information visually on a computer monitor or other suitable display.

By way of example, a tree-viewer program could be written to present graphically on a computer monitor a display of all or part of the tree structure. The program could provide various user options. For instance, the program could provide a FIND MOLECULE option that may allow prompt a user to enter a specific molecule ID or molecule description and may then responsively search the tree and visually present all nodes of the pyramid that contain (represent) the specified molecule. As another example, the program could provide EXPAND and CONTRACT options for each cluster, which may allow a user to selectively expand or contract a display of the tree so as to selectively see only a particular sub-tree. As yet another example, the program could allow a user to selectively view specified attributes of a given cluster or clusters. One such attribute may be the learned_key, presented as a chemical formula for instance.

In an exemplary embodiment, each node can be color coded (or otherwise emphasized) for display, with a color indicative of the difference between its average activity level (of the molecules it contains) and the average activity level of its parent node. This color coding thus conveniently defines whether, based on the computer's analysis, the pharmacophore (filter/key) that gave rise to a given node is activity-enhancing or activity-detracting. Presentation of these conclusions in such a visually simple fashion is a great advantage, particularly when the input data set represents a vast amount of information that a chemist could quite likely not manually interpret.

A tree generated in the manner described above can beneficially embody structurally parsed indicia of each molecule in the input data set. Such information readily indicates through lineage in the tree the structurally important keys of each molecule, and how each key can progress to provide varying levels of activity. After the root node, each parent node in the tree that leads to multiple children nodes usefully provides an indication of how the common substructure (key) defining the parent node can be modified in practice to achieve a different pharmacophoric mechanism. By tracing the lineage toward the root of the tree from any given node, one can readily determine a composite substructure that is likely to be responsible for classifying the family of molecules in the given node.

Phrased another way, in practice, the tree structure provides information to the end-user chemists in both its intermediate and terminal nodes. The intermediate levels (parent nodes) can be used to describe family resemblances among the molecules that are in descendent nodes of that parent. This gives a more coarse level of description about what is similar among the molecules contained in that node or its descendents. The farther one progresses down into the tree, the more detailed and finer-grained the differences are that are drawn between groups of molecules.

A chemist may thus review the tree structure and conveniently see different ways to modify a molecule so as to perhaps achieve different levels of activity. Further, the computer can be programmed to depict for a chemist a core chemical structure as defined by a parent node in the tree, together with options of structural variations that may be likely to give rise to various levels of activity.

In addition, it is possible that, when generating the tree structure, at one or more nodes, some molecules in the node may not match any of the children filters. Smaller molecules, for instance, are likely to reach this point as the tree grows larger, since the computer will likely begin to find larger keys for which the smaller molecules do not have a match. In an exemplary embodiment, the computer may effectively "drop" such molecules from further analysis. However, the computer also preferably stores in the node an indication of such "dropped" molecule(s) and may provide that valuable information as output a chemist.

The computer may provide as output some or all of the information that it has gleaned in its analysis of the input data set. For instance, the computer can provide a description of the entire tree structure. Alternatively, for instance, the computer can provide a description of only one or more nodes or groups of nodes. In addition, the computer can provide its output entirely once it has finished growing the tree and/or while it grows the tree. For example, each time the computer explores a new node, the computer can output its findings.

xi. Testing the Phylogenetic-Like Tree

In accordance with an exemplary embodiment, the computer can be programmed further to test the resulting tree structure in order to evaluate the efficacy of the structure-to-activity relationships represented by the tree. One way to test the tree is to feed through the tree some or all of the inactive molecules from the input data set, i.e., those molecules that were not chosen for inclusion in the training set. Some or all of the inactive compounds may flow through the tree (beginning with the root node) and land in one or more terminal nodes of the tree. This can be significant information for a chemist.

For example, if a given terminal node of the tree includes only highly active molecule(s), absent testing, it may be reasonable to conclude that the learned key that gave rise to that node correlates with the high activity level. However, if, for example, 30 inactive molecules fall into the same node, an expert may rightly conclude that the node was a false positive, i.e., the learned key of the node is not truly representative of high activity level. The computer may thus output an indication accordingly. The indication may, for instance, signal a need to use some other types of descriptors that could better correlate with activity. For example, if the computer system employed a set of only 2-dimensional descriptors (e.g., not considering 3D orientation), a reasonable conclusion may be that the computer should employ a set of 3D descriptors. Alternatively, this result may lead to a decision to re-screen and/or to expand the library in that area so as to enable finer-level discrimination.

xii. Post-Processing Activity:

Applying the Tree as a Multi-Domain Classifier.

Once the computer has fully created the tree structure, it is finished learning. The tree structure may then usefully serve as a multi-domain classifier, to provide additional useful information to a chemist or other person.

At this stage, the computer may run a set of test molecule(s) through the tree to determine whether and where the test molecule(s) land within the tree. The test molecules could be molecules that have an unknown activity level, i.e., molecules that have not been subjected to the assay(s) to which the molecules of the training set were subjected. A given test molecule may fit neatly within one of the nodes of the multi-domain classifier, which may support a conclusion that the molecule is likely to have an activity level similar to that indicated by the node (i.e., similar to the average activity level of the training molecule(s) that defined the "actives" attribute of the node).

On the other hand, a given test molecule may not fit within any node of the classifier. If that happens, the computer may deem such a molecule to be an outlier and may output an indication accordingly. The identification of outliers is a significant outcome, particularly if the test molecule turns out to be an active molecule.

Of course the computer may perform other testing and post-processing functions as well with respect a tree structure generated in accordance with the present invention.

C. Exemplary Pseudo-Code

Although the foregoing description of an exemplary embodiment will enable a person of ordinary skill in the art to readily make and use the invention, the following exemplary pseudo-code listing is provided for additional understanding. It should be understood that this pseudo-code depicts only one or more possible methods of carrying out an exemplary embodiment of the invention (and may differ in some respects from the description provided above). The pseudo-code is not intended to be limiting in any respect.

In this pseudo-code listing, the number of molecules in an exemplary data set is n, the number of original keys is m, and each key is weighted with a value of 1.

---

Exemplary Pseudo-Code Listing
Copyright © 1999, 2000 Bioreason, Inc.

1. Choose a training set
2. Create a feature vector describing each molecule in the training set
   For every molecule in the training set, molecule$_y$, where y increments from 1 to n:
       Initially create a zero-length feature vector, which will hold one integer for each key describing molecule$_y$
       For every original substructure key, original_key$_z$, where z increments from 1 to m:

---

Exemplary Pseudo-Code Listing
Copyright © 1999, 2000 Bioreason, Inc.

Search the Daylight SMILES representation of molecule$_y$ with the Daylight SMARTS representation of the original_key$_z$.
      Append the number of matches (of original_key$_z$ to molecule$_y$) to the feature vector.
  End for all substructure keys, original_key$_z$.
  Create an empty bit vector, bit_vector$_y$, for molecule$_y$.
  For every feature in the feature vector, feature$_x$, where x increments from 1 to m:
      If feature_vector$_x$ is greater than zero then:
          Set bit_vector$_x$ to 1
      Else:
          Set bit_vector$_x$ to 0
      End for all features.
End for all molecules.
3. Initialize a directed graph data structure
  Create a directed graph data structure, initialized to an empty graph
4. Initialize a node data structure (the first/root node of the tree)
  For every molecule in the training set selected to use for generating the phylogenetic-like tree
      Get the molecule's id
      Append the id to a "training-molecules" list created for this purpose
  End for all molecules
  Create a node data structure
  Initialize the following attributes of the node as follows to make it the root_node:
      Set the "key" attribute to 0 to indicate that this node data structure is the root node of the phylogenetic-like tree to be generated.
      Set the "actives" attribute list to the "training-molecules" list prepared previously
5. Choose node to explore for growing the phylogenetic-like tree
  5.1  Create list of all candidate leaf nodes for growing the phylogenetic-like tree
      Initialize a go-node list to empty.
      If there are nodes which have no status
          For every node A with no status:
              If the number of molecules it contains (i.e. the length of the "actives" list of the node) is less than x, where x is a number specified by the user such as 21, then set the status of node A to "stopped" and indicate that it is too small.
              If the length of the "actives" list of node A is the same as the length of the "actives" list of its parent, then set the status of A to "stopped" and indicate that A is a duplicate of its parent.
              Or if the "learned_key" attribute of node A is a substructure of the "learned_key" attribute of its parent, then set the status of A to "stopped" and indicate that the learned key of A is a substructure of the learned key of one of its ancestors.
              If the "learned_key" attribute of node A is a substructure of the "learned_key" of another candidate leaf node B, then set the status of node A to "stopped" and indicate that it is a substructure of node B and indicate that node B is a superstructure of node A.
      End for all nodes with no status
      For every node A that is not "stopped"
          Label node A as "go node"
          Add node A to the go-node list
          Find and mark each node B which is a duplicate of node A:
              If the list of "actives" of node A is exactly the same as the list of "actives" of any other node B in the tree, then indicate that A and B are duplicates of one another.
      End for all nodes with no status
  5.2  Pick the node to grow the tree according to the growth method specified by the user
      If the go-node list is empty, then return nothing, tree has been completed. (Note: This is a stopping condition for -continued Exemplary Pseudo-Code Listing
Copyright © 1999, 2000 Bioreason, Inc.

```
    tree creation.)
    Else for each node in the go-node list:
        If the phylogenetic-like tree growth method selected by
        the user is "BFS" then:
            Sort all go nodes with respect to depth
            in a list N1 in ascending order.
            Sort the set of nodes with the smallest depth
            from list N1 with respect to the number of
            atoms that their "learned_key" attribute has
            in a list N2 in ascending order.
            Select the first node N from list N2.
            If the status of N reveals that it has duplicates,
            i.e. other go nodes with the same compound sets,
            then change those go nodes to stopped nodes
            Return node N
        Else if the phylogenetic-like tree growth method
        selected is "DFS" then:
            Sort all go nodes with respect to depth in a list
            N1 in descending order.
            Sort the set of nodes with the largest depth from
            list N1 with respect to the number of atoms that
            their "learned_key" attribute has in a list
            N2 in ascending order.
            Select the first node N from list N2.
            If the status of N reveals that it has duplicates,
            i.e. other go nodes with the same compound sets,
            then change those go nodes to stopped nodes
            Return node N
        Else if the phylogenetic-like tree growth method
        selected is "DivFS" then:
            Compute the diversity of each go node by,
            for example, calculating the Tanimoto distance
            between each pair of molecules in the actives
            attribute list of the go node and taking
            the average
            Sort all go nodes with respect to diversity in a
            list N1 in descending order.
            Sort the set of nodes with the largest diversity
            from list N1 with respect to the number of atoms
            that their "learned_key" attribute has in a
            list N2 in ascending order.
            Select the first node N from list N2.
            If the status of N reveals that it has duplicates,
            i.e. other go nodes with the same compound sets,
            then change those go nodes to stopped nodes
            Return node N
6.  Clustering the molecules using a clustering method
    defined by the user
    Using the feature vector describing each molecule, cluster
    the active molecules of the data set specified by the "actives"
    attribute of node N in a k by k self organizing map, to establish
    a trained self organizing map.
7.  Identify hotspots in the self organizing map
    Initialize a count of hot spot clusters, p, to 0.
    For each cluster in the trained self organizing map:
            If the cluster contains more than J (e.g., 4) active
            molecules then identify this cluster as a hotspot and
            increase the count of hotspot clusters, p, by 1.
    End for each cluster in the self organizing map
8.  Learn new keys
    For each of the clusters identified as hotspots, cluster_q,
    where Q runs from 1 to p:
            Apply a genetic algorithm to find the common
            substructures of all the molecules in the
            hotspot cluster.
            Designate the largest common substructure as a
            proposed new substructure key, and add it to a set
            of proposed, unique, new substructure keys,
            called the l-keys list.
    End for each of the clusters, cluster_q, identified as a hotspot.
9.  Update Phylogenetic-like Tree
    Set the attribute "learned_keys" of the node N under
    growth to equal the list l-keys of proposed new substructure
    keys produced in step 8.
    Create a new list l-molecules
    For each key k in the l-keys list of node N, (parent node):
```

-continued

Exemplary Pseudo-Code Listing
Copyright © 1999, 2000 Bioreason, Inc.

```
            If k is a non-empty substructure then:
                Increment the node counter c of the phylogenetic-
                like tree by 1
                For each molecule m included in the actives
                attribute list of the parent node N
                    Search the Daylight SMILES representation
                    of m with the Daylight SMARTS
                    representation of the key k
                    If the key k is found at least once in
                    molecule m, then append molecule m to
                    the l-molecules list
                End for each molecule m.
                Create a new node N_new, with id equal to
                the counter c, SMARTS (learned_key) equal
                to k and actives list equal to the l-molecules
                list.
                Grow the phylogenetic-like tree by appending
                the arc between parent node N and child
                node N_new.
        End for each key k in the learned_keys list of node N
        Set status of node N to "explored", indicating that all
        operations on the node were completed successfully
10. Iterate
    Repeat the process, starting at step 5 until stop condition
    (in step 5.2) is met.
``` d. Exemplary Advantages

The exemplary embodiment described above is adaptive to the data set of molecules being analyzed. In the context of chemical or biological analysis, the new learned keys are derived from the clustering done on the molecules that end up in a particular hotspot. The key is thus customized to that particular set of molecules, and its derivation contains valuable information for the screening chemist. Some of the unique and valuable results from this system include (i) the extraction of this information via the lineage of the learned keys, and (ii) the information about the set of molecules that end up together at the end of a particular branch.

The invention advances over the existing art in many useful ways. By way of example and without limitation, the invention reduces the vast amount of information generated in an original screen (e.g., HTS) into several accessible decision points that a chemist can visually inspect and analyze.

As another example, unlike the classification model of the RP system, which is guided principally by knowledge of the response variables, the present system is advantageously guided by inherent groupings and similarities within the structure of the data itself. In a preferred embodiment, the present invention does not group molecules by activity (e.g., responses to targets) as does the RP system. Rather, the preferred embodiment groups molecules according to their structural similarities.

As yet another example, a preferred embodiment of the invention enables individuals (e.g., molecules) to fall into more than one categorization or subclass. The branch points generated by a computer system in the preferred embodiment are filters through which each molecule may either pass or not pass. In contrast, the RP system divides individuals at every branch-point into the "haves" and the "have nots," which necessarily misses valuable information. In order to generate more than one path for a specific molecule or set of molecules, the RP system must run a great many times, using techniques such as surrogate splits or variable elimination (e.g., via backwards elimination). Performing these techniques and analyzing the results can unfortunately be very time consuming.

As a further example, a preferred embodiment of the invention facilitates robust determination of pharmacophoric families. With the RP system, the building of a hierarchical tree structure is based on a predefined set of descriptors, and it is those descriptors that define the common substructure of each node of the tree. In this sense, RP does not discover new pharmacophoric mechanisms (e.g., substructures). In a preferred embodiment of the present invention, however, branch points in the tree are defined by adaptively learned keys based on the structures of the compounds used to build the tree.

Still additionally, as noted above, the noise level of responses from HTS screening may contribute to compromised or faulty splitting decisions in an RP tree. Advantageously, a computer system operating in accordance with a preferred embodiment is built on similarities among the features of the molecules and is not directly related to the measure of activity reported by the response variable or to predefined classes of active and inactive compounds.

Further, the presently preferred trees are designed in such a way that identifying suspected false positives and false negatives in the data is straightforward. The computer system may conclude that inactive molecules that fall into tightly defined classes of active molecules, particularly at the terminal nodes, and that cannot be distinguished from actives using further analysis, are potential false negatives, for example.

The preferred embodiment categorizes molecules in as many ways as discoverable with neural-network clustering. This is an advance over the existing art, which only partitions the data into discrete branches of a tree. With the benefit of the present invention, it is possible for some molecules to proceed down more than one branch of the tree at once. Thus, a single molecule can end up in more than one "leaf" node of the tree. In practice, this can signal to a chemist that a single molecule has two different possible mechanisms of interaction or more than one interactive domain, or more than one avenue for optimization. Categorizing the molecules in more than one way allows the chemist to see relationships among molecules from more than one perspective, which in practice can lead to insights that would not be possible with existing analysis systems.

As a related point, a preferred embodiment of the invention can advantageously provide information about core structural areas in a molecule even if non-contiguous; i.e., the preferred embodiment facilitates finding non-contiguous common substructures or pharmacophores in a set of molecules. The computer system may output a signal indicating such non-contiguous substructures. For instance, the computer system may provide a display highlighting the parts of the molecules that are involved in the keys that led to each end node/leaf, which will readily reflect the presence of more than one region of similarity in the set of molecules.

e. Exemplary Configuration

An exemplary embodiment of the present invention can be carried out by appropriately configured analog circuitry and/or by a programmable or dedicated processor running an appropriate set of machine language instructions (e.g., compiled source code) stored in memory or other suitable storage medium. As noted above, those or ordinary skill in the art will be able to readily prepare such circuitry and/or code, provided with the foregoing description.

3. Multi-Domain Classification of Chemical Structures

In another respect, an exemplary embodiment of the present invention provides a computer-based system for multi-domain classification of chemical structures (or other such graphs). In this regard, for instance, the system involves the functions of (i) creating in a computer memory a hierarchical tree structure having nodes defined by (or defining) chemical substructures (subgraphs) and then (ii) filtering a test set of chemical structures (graphs) through the tree structure so as to classify the test set into the nodes defined by the tree.

More specifically, using chemical structures as the example of graphs (and chemical substructures as examples of subgraphs), the system can involve the following functions to build a phylogenetic-like tree:

1. Receiving into a data storage medium (e.g., a computer memory) a set of data representing a number of chemical compounds, at least a plurality of which will be used as training compounds in the following steps;

2. Establishing a characterization (i.e., description or representation) of each compound, based on an initial set of descriptors;

3. Based on the characterizations of the compounds, hierarchically clustering the compounds (i.e., their data representations) so as to form in a data storage medium a hierarchical tree structure of compound clusters, where each cluster represents one or more of the compounds;

4. During or after the tree-formation process, learning for each of at least a plurality of the compound clusters a substructure that is common to the compound(s) represented by the cluster, where the substructure is not one of the descriptors in the initial set of descriptors.

The resulting tree structure thus preferably defines a root node (representing all of the training compounds), defining a first generation (i.e., level) of the tree. The root node has a number ($\tau$ 1) of children nodes (each representing one or more of the training compounds), cooperatively defining a second generation of the tree. Each child node in turn has a number of children nodes (each also representing one or more of the training compounds), cooperatively defining a third generation of the tree. This structure continues iteratively, extending to a number of terminal or "leaf" nodes that have no children. Each node of the tree structure has associated with it a learned substructure that represents a commonality among the compounds that formed the node. For at least a plurality of the nodes (and preferably for every node), the common substructure is not one of the predefined descriptors used initially to characterize the molecules.

In a further preferred aspect, the computer assigns to each node of the tree an activity attribute representative of the activity levels of the compound(s) that are represented by the node. Any metric can be applied to generate this representative activity level. As a simple example, the representative activity level can be the average of activity levels of the training compounds that are represented by the node.

Once this tree structure is established, the training compounds that were hierarchically clustered to form the tree can be disregarded (for the following purpose). What remains is then a hierarchical tree structure of chemical substructures. At least each node of the tree structure after the root node defines a respective learned chemical substructure.

This hierarchical tree of chemical structures can then be used as a multi-domain classifier. In particular, the learned substructure of each node can be used as a filter to determine whether a given compound can be classified in that node. If a compound includes that common substructure defined by the node, the compound (i.e., a data representation of the compound) can fall within the node.

Thus, the hierarchical tree of chemical structures can be applied as a multi-domain classifier to classify a set of test compounds (either new data not part of the original input data set, or some subset of the original data set). Beginning with the root node (representing all of the test compounds), this aspect of the system may involve the following functions:

1. With respect to each compound in the root node (generation 1 of the tree):
   a. For each node in generation 2, determine whether the compound includes the learned substructure defined by the node in generation 2.
   b. If so, classify the compound into that node in generation 2.
   c. If not, do not classify the compound into that node in generation 2.
2. With respect to each node in generation 2 that represents at least one test compound,
   a. With respect to each compound in the node in generation 2,
      i. For each node in generation 3, determine whether the compound includes the learned substructure defined by the node in generation 3.
      ii. If so, classify the compound into that node in generation 3.
      iii. If not, do not classify the compound into that node in generation 3.
3. Iteratively repeat the process of step 2 to classify into each subsequent generation of the phylogenetic-like tree.

The training compounds and test compounds may all be represented by the same input data set, such as data resulting from the same HTS assay. For instance, provided with an input data set representing chemical structures and activity measurements (such as described above), a computer can select as the training set all of the active compounds represented by the input data or some subset of all of the represented active compounds, and the computer can select as the test set others of the active compounds or some or all of the inactive compounds. Alternatively, the training set could be represented by one input data set and the test set could be represented by another input data set.

By generating the multi-domain classifier based on the actives and then filtering the inactives through the classifier, the computer can reach some commercially useful conclusions, which it can present to a chemist. An example of such a conclusion was described above in the context of testing the efficacy of the exemplary tree structure. In particular, if many inactive molecules fall into a particular node, this may signify that the node was a false positive, and the computer may output an indication accordingly.

Further, as mentioned above, the test set could include compounds whose activity levels are unknown. In that case, the multi-domain classifier can be applied as an activity-predictor. If a compound filters through the tree and fits neatly within a terminal node that has a high representative activity level, it might be reasonable to conclude that the compound is likely to have about that same activity level if subjected to the same assay(s). In addition, if a compound does not fit within any node of the classifier, the compound might be deemed to be an outlier. In either case, the computer can output an indication accordingly.

The process of building the multi-domain classifier (tree of chemical structures) involves hierarchically clustering the chemical compound structures (i.e., clustering their data representations). This clustering function can take any desired form and may, or may not, integrally include the function of establishing a learned chemical substructure for each node of the classifier.

One example of a suitable hierarchical clustering technique is that described above.

Generally speaking, this example includes iteratively (i) grouping the chemical structures at a given generation based on their descriptor vectors, (ii) learning new substructures, such as an MCS, from each group, (iii) applying the newly learned substructures as filters to create children defining a next generation, and (iv) repeating from step (i).

Without limitation, other examples of suitable clustering techniques, together with generation of common substructure filters, include the following:

1. A computer may agglomeratively cluster the chemical structures into a pyramid, from the ground up. I.e., begin with singleton clusters and merge clusters together based on similarity of the compounds, continuing sequentially until reaching a root node (tip of the pyramid) that represents all of the compounds. After completing the agglomeration (or as each cluster is established), the computer may analyze the compounds represented by each cluster and determining a representative common substructure (e.g., MCS), which the computer may assign as the defining substructure for that cluster (node) of the classifier.

2. A computer may agglomeratively cluster the chemical structures into a pyramid, based on similarity of the compounds. As the pyramidal clustering process progresses, it will involve comparing the similarity within pairs of entities and merging together the most similar entities. Each entity may be a compound or a cluster of compounds. To determine the similarity between any two such entities, the process may involve identifying a maximum common substructure between the two entities. (E.g., as between a cluster and a compound, the process may find the largest chemical substructure common to (i) the compound and (ii) a representative (e.g., maximum common) substructure of the cluster). To identify the most similar pair (to be merged into a new cluster), the computer may then select a largest of the maximum common substructures (e.g., the one with the most atoms). The computer may then assign as the representative substructure for a resulting merged cluster the maximum common substructure of the merged pair.

3. As in the RP method described in the background section above, a computer may divisively cluster (i.e., from top down) a set of chemical structures based on structural descriptors. With respect to each node, the computer may identify one of the predefined descriptors that best divides the set of chemical structures of that node into two children having between them a maximum difference in activity. As presently contemplated, the computer may then (or as the process progresses) identify for each node a significant common substructure (e.g., MCS) and assign that substructure as the representative substructure for that node of the resulting classifier.

With each of these or other techniques, the compounds that are clustered to form the hierarchical tree structure that is the multi-domain classifier can be effectively removed from the classifier after the tree is built. Of course, data representations of the training set may alternatively remain associated with the respective nodes and may be provided as output as well, if desired.

In any hierarchical clustering technique that is based on comparisons of descriptor vectors representing the chemical structures, the members of the descriptor vectors can be bit keys defining the presence or absence of predefined substructures. Each substructure can be represented in any suitable way, such as, without limitation, MACCS keys, BCI (Barnard Chemical Informatics) keys, or Daylight fingerprint keys, each of which are well known to those skilled in the art.

Further, in any hierarchical clustering technique that is based on evaluation of similarity between two entities (such as between two compounds, or two clusters of compounds, or a compound and a cluster of compounds), any desired metric can be used to determine the similarity (or, equivalently as a matter of perspective, dissimilarity). As examples, and without limitation, similarity metrics include Tanimoto distance, Euclidean distance, Cosine coefficient, and Tversky coefficient.

A computer programmed to perform multi-domain chemical structure classification as presently contemplated can provide a set of output data indicating the classifications established according to the classifier. This output could be provided graphically, as a depiction of the tree structure via a tree-viewer for instance, or it could take any other desired form. Preferably, at least a portion of the output will consist of descriptions of the resulting classification(s).

4. Conclusion

An exemplary embodiment of the present invention has been described herein. It will be understood, however, that changes and modifications may be made thereto without deviating from the true spirit and scope of the invention as defined by the claims. For instance, where appropriate, individual elements described herein may be substituted with other equivalent elements now known or later developed. All examples described herein are illustrative and not necessarily limiting.

Further, the claims should not be read as limited to the described order of elements unless stated to that effect. In addition, use of the term "means" in any claim is intended to invoke 35 U.S.C. § 112, paragraph 6, and any claim without the word "means" is not so intended.

We claim:

1. A method for screening a set of molecules, in order to assist in identifying sets of molecular features that are likely to correlate with specified activity, each molecule having a feature characteristic and an activity characteristic, the method comprising, in combination:
   (a) with respect to the molecules:
      (i) defining groups of the molecules based on similarity of the feature characteristics of the molecules,
      (ii) selecting one or more of the groups defined in the preceding step based on the activity characteristics of the molecules in the groups,
      (iii) for each group selected in the preceding step identifying a feature set common to all molecules in the group, and
      (iv) for each feature set identified in the preceding step, (A) selecting from the molecules a number of molecules that exhibit the feature set, (B) establishing a new set of molecules consisting of the number of molecules, (C) deciding whether to recursively repeat the method with respect to the new set of molecules, and, if so, (D) repeating steps (i)–(iv) with respect to the new set of molecules; and
   (b) providing a description of at least one new set of molecules established in step (iv), the description including a first portion indicating the feature set for which the new set of molecules was established and a second portion indicating the activity characteristics of the molecules in the new set of molecules,
   whereby the first and second portions may cooperatively establish a correlation between molecular features and molecular activity.

2. A method as claimed in claim 1, wherein the set of molecules consists of molecules determined to have at least a designated activity characteristic.

3. A method as claimed in claim 1, wherein the activity characteristic is multi-dimensional.

4. A method as claimed in claim 1, wherein defining groups of the molecules based on similarity of the feature characteristics of the molecules comprises (i) establishing for each molecule a feature vector based on the feature characteristic of the molecule, and (ii) clustering the feature vectors of the molecules based on similarity of the feature vectors.

5. A method as claimed in claim 4, wherein each feature vector is keyed to structural descriptors, and wherein each of the structural descriptors is selected from the group consisting of (i) a MACCS key, (ii) a BCI key, and (iii) a Daylight fingerprint key.

6. A method as claimed in claim 4, wherein clustering the feature vectors comprises applying a clustering process selected from the group consisting of (i) self-organizing map, (ii) agglomerative clustering, and (iii) divisive clustering.

7. A method as claimed in claim 6, wherein the clustering process uses a similarity measure selected from the group consisting of (i) a Euclidean distance, (ii) a Tanimoto distance, (iii) a Tversky coefficient, (iv) a Euclidean-Soergel product, and (v) a Euclidean-Tanimoto product.

8. A method as claimed in claim 6, wherein clustering the feature vectors comprises applying a self-organizing map.

9. A method as claimed in claim 6, wherein clustering the feature vectors comprises applying an agglomerative clustering process selected from the group consisting of (i) Wards, (ii) complete-link, (iii) average link, (iv) single link, and (v) centroid.

10. A method as claimed in claim 6, wherein clustering the feature vectors comprises applying a divisive clustering process selected from the group consisting of (i) recursive partitioning, (ii) DIANA algorithm, and (iii) MONA algorithm.

11. A method as claimed in claim 6, wherein the clustering process produces a number of clusters, and wherein each group of molecules comprises a cluster selected from the number of clusters.

12. A method as claimed in claim 6, wherein the clustering process produces a number of clusters, and wherein each group of molecules comprises a metacluster derived from the number of clusters.

13. A method as claimed in claim 12, further comprising selecting the metacluster by a process selected from the group consisting (i) Kelley method, (ii) point-biserial method, (iii) Hubert's Gamma method, and (iv) Fagan's method.

14. A method as claimed in claim 1, wherein selecting one or more of the groups of molecules comprises selecting groups having at least a threshold concentration of a specified activity characteristic.

15. A method as claimed in claim 1, wherein identifying a feature set common to all molecules in a group comprises identifying a chemical structure present in all molecules in the group.

16. A method as claimed in claim 15, wherein the chemical structure comprises an arrangement of atoms and bonds.

17. A method as claimed in claim 16, wherein the arrangement of atoms and bonds is a contiguous arrangement.

18. A method as claimed in claim 1, wherein identifying a feature set common to all molecules in a group comprises identifying a 2D substructure common to all of the molecules in the group.

19. A method as claimed in claim 18, wherein identifying a 2D substructure common to all of the molecules in the group comprises applying a process selected from the group consisting of (i) an exhaustive maximum common substructure search, (ii) a genetic algorithm common substructure search, (iii) a weighted exhaustive maximum common substructure search, and (iv) a weighted genetic algorithm maximum common substructure search.

20. A method as claimed in claim 1, wherein identifying a feature set common to all molecules in a group comprises identifying a 3D substructure common to all of the molecules in the group.

21. A method as claimed in claim 1, wherein identifying a feature set common to all molecules in a group comprises identifying a largest chemical substructure common to all molecules in the group.

22. A method as claimed in claim 21, wherein identifying a largest chemical substructure common to all of the molecules in the group comprises applying a genetic algorithm.

23. A method as claimed in claim 21, wherein identifying a largest chemical substructure common to all of the molecules in the group comprises exhaustively searching for and identifying common substructures among the molecules in the group and selecting the largest chemical substructure from the identified common substructures.

24. A method as claimed in claim 21, wherein identifying a largest chemical substructure common to all of the molecules in the group comprises comparing graphs of the molecules in the group.

25. A method as claimed in claim 1, wherein selecting from the molecules a number of molecules that exhibit the feature set comprises selecting all of the molecules that exhibit the feature set, wherein all of the molecules is one or more molecules.

26. A method as claimed in claim 1, wherein providing a description of at least one new set established in step (iv) comprises displaying a tree structure comprising a root node reflecting the data set and descendent nodes reflecting new data sets established in step (iv).

27. A method as claimed in claim 1, wherein the description further comprises a third portion indicating a measure of activity differential between a pair of feature sets for which successive new data sets were established.

28. A method for screening a data set representing a plurality of molecules, in order to assist in identifying sets of molecular features that are likely to correlate with specified activity, the data set defining, for each represented molecule, a feature characteristic and an activity characteristic, the method comprising, in combination:
  (a) with respect to the molecules represented by the data set:
    (i) defining groups of the molecules based on similarity of the feature characteristics of the molecules,
    (ii) selecting one or more of the groups defined in the preceding step based on the activity characteristics of the molecules in the groups,
    (iii) for each group selected in the preceding step, identifying a feature set common to all molecules in the group, and
    (iv) for each feature set identified in the preceding step, (A) selecting from the molecules a number of molecules that exhibit the feature set, (B) establishing a new data set representing the number of molecules, (C) deciding whether to recursively repeat the method with respect to the new data set, and, if so, (D) repeating the method from step (i) with respect to the molecules represented by the new data set; and
  (b) providing a description of at least one new data set established in step (iv), the description including a first portion indicating the feature set for which the new data set was established and a second portion indicating the activity characteristics of the molecules represented by the new data set,
  whereby the first and second portion may cooperatively establish a correlation between molecular features and activity.

29. A method as claimed in claim 28, wherein the plurality of molecules represented by the data set consists of molecules determined to have at least a designated activity characteristic.

30. A method as claimed in claim 28, wherein the activity characteristic is multi-dimensional.

31. A method as claimed in claim 28, wherein defining groups of the molecules based on similarity of the feature characteristics of the molecules comprises (i) establishing for each molecule a feature vector based on the feature characteristic of the molecule, and (ii) clustering the feature vectors of the molecules based on similarity of the feature vectors.

32. A method as claimed in claim 31, wherein clustering the feature vectors comprises applying a self-organizing-map.

33. A method as claimed in claim 32, wherein each group of molecules comprises a cluster of the self-organizing map.

34. A method as claimed in claim 32, wherein at least one group of molecules comprises a metacluster of the self-organizing map.

35. A method as claimed in claim 31, wherein clustering the feature vectors comprises applying Wards clustering.

36. A method as claimed in claim 28, wherein selecting one or more of the groups of molecules comprises selecting groups having at least a threshold concentration of a specified activity characteristic.

37. A method as claimed in claim 28, wherein identifying a feature set common to all molecules in a group comprises identifying a chemical structure present in all molecules in the group.

38. A method as claimed in claim 37, wherein the chemical structure comprises an arrangement of atoms and bonds.

39. A method as claimed in claim 38, wherein the arrangement of atoms and bonds is a contiguous arrangement.

40. A method as claimed in claim 28, wherein identifying a feature set common to all molecules in a group comprises identifying a largest chemical substructure common to all molecules in the group.

41. A method as claimed in claim 40, wherein identifying a largest chemical substructure common to all of the molecules in the group comprises applying a genetic algorithm.

42. A method as claimed in claim 40, wherein identifying a largest chemical substructure common to all of the molecules in the group comprises exhaustively searching for and identifying common substructures among the molecules in the group and selecting the largest chemical substructure from the identified common substructures.

43. A method as claimed in claim 40, wherein identifying a largest chemical substructure common to all of the molecules in the group comprises comparing graphs of the molecules in the group.

44. A method as claimed in claim 28, wherein selecting from the molecules a number of molecules that exhibit the feature set comprises selecting all of the molecules that exhibit the feature set, wherein all of the molecules is one or more molecules.

45. A method as claimed in claim 28, wherein providing a description of at least one new data set established in step (iv) comprises displaying a tree structure comprising a root node reflecting the data set and descendent nodes reflecting new data sets established in step (iv).

46. A method as claimed in claim 28, wherein the description further comprises a third segment indicating a measure of activity differential between a pair of feature sets for which successive new data sets were established.

47. A computer-readable medium embodying a set of machine language instructions executable by a computer for performing the method steps of claim 28.

48. A method for screening a data set representing molecules, the data set defining, for each represented molecule, a feature characteristic and an activity characteristic, the method comprising, in combination:
(a) selecting from the data set at least one group of molecules that have similar feature characteristics and that cooperatively represent a particular activity characteristic, said group of molecules having a set of discriminating features defining similarity of the molecules in said group;
(b) for each of the at least one group selected in the preceding step, identifying at least one common subset of features of the molecules in each group based at least in part on a measure of how much said at least one common subset of features participated in defining the discriminating features of said group;
(c) for each common subset of features identified in the preceding step, establishing a new data set representing those molecules from the data set that include the common subset of features;
(d) selecting from the new data set at least one group of molecules that have similar feature characteristics and that cooperatively represent a particular activity characteristic, each of said at least one group of molecules having a set of discriminating features defining similarity of the molecules in said group;
(e) for each of the at least one group selected in the preceding step, identifying at least one common subset of features of the molecules in each group based at least in part on a measure of how much said at least one common subset of features participated in defining the discriminating features of said group; and
(f) outputting data indicative of at least one common subset of features.

49. A computer-readable medium embodying a set of machine language instructions executable by a computer for performing the method steps of claim 48.

50. A processing system for screening a data set representing a plurality of molecules, in order to assist in identifying sets of molecular features that are likely to correlate with specified activity, the data set defining, for each represented molecule, a feature characteristic and an activity characteristic, the processing system comprising, in combination:
(a) means for performing the following method steps with respect to the molecules represented by the data set:
(i) defining groups of the molecules based on similarity of the feature characteristics of the molecules,
(ii) selecting one or more of the groups defined in the preceding step based on the activity characteristics of the molecules in the groups,
(iii) for each group selected in the preceding step, identifying a feature set common to all molecules in the group, and
(iv) for each feature set identified in the preceding step, (A) selecting from the molecules a number of molecules that exhibit the feature set, (B), establishing a new data set representing the number of molecules, (C) deciding whether to recursively repeat the functions with respect to the new data set, and, if so, (D) repeating from step (i) with respect to the molecules represented by the new data set; and (b) means for providing a description of at least one new data set established in step (iv), the description including a first segment indicating the feature set for which the new data set was established and a second segment indicating the activity characteristics of the molecules represented by the new data set,
whereby the first and second segments may cooperatively establish a correlation between molecular features and activity.

51. A computerized method of converting a set of data representing a plurality of molecules into a data structure representing pharmacophoric mechanisms, the set of data defining respectively for each molecule a structure and an activity characteristic, a node in a data storage medium representing the plurality of molecules, the method comprising, in combination:
(a) grouping the molecules of the node into a plurality of groups based on structural similarity of the molecules;
(b) selecting one or more of the groups established in element (a) based on the activity characteristics of the molecules in the groups;
(c) for each group selected in element (b), identifying a common substructure among the molecules in the group, the common substructure defining a pharmacophoric mechanism;
(d) for each common substructure identified in element (c),
(i) selecting from the molecules of the node at least one molecule that includes the common substructure, and establishing a child node representing the at least one selected molecule;
(ii) determining whether to expand the data structure from the child node, and, if so, repeating the method from step (a) with the node being the child node; and
(e) outputting an indication of at least a portion of the data structure including an indication of at least one pharmacophoric mechanism.

52. A method as claimed in claim 51, wherein selecting one or more of the groups established in element (a) comprises selecting a plurality of the groups established in element (a).

53. A method as claimed in claim 51, wherein outputting an indication of at least a portion of the data structure comprises outputting a description of the data structure.

54. A method as claimed in claim 53, wherein outputting a description of the data structure comprises providing an output display selected from the group consisting of a graphical display, a textual display, and a combination graphical-textual display.

55. A method as claimed in claim 51, wherein outputting an indication of at least a portion of the data structure comprises outputting a description of at least one node of the data structure.

56. A method as claimed in claim 55, the description of the at least one node comprises information selected from the group consisting of the molecules represented by the node, the common substructure represented by the node, and an activity characteristic measure based on the activity characteristics of the molecules represented by the node.

57. A method as claimed in claim 56, wherein the at least one node comprises a child node stemming from a parent node, and wherein the description of the child node comprises an activity characteristic differential representing a difference in activity level from the parent node to the child node.

58. A method as claimed in claim 51, wherein the common substructure identified in element (c) comprises a substructure selected from the group consisting of a contiguous structure of atoms and bonds and a non-contiguous structure of atoms and bonds.

59. A method as claimed in claim 51, wherein the common substructure identified in element (c) comprises a non-contiguous structure of atoms and bonds.

60. A method for building a multi-domain molecular classifier, the method comprising in combination:
(a) receiving a set of data representing a set of molecules;
(b) deriving one or more pharmacophores from the set of data, each pharmacophore defining a node of a multi-domain classifier;
(c) using each pharmacophore respectively as a filter to establish a new set of data representing a subset of the molecules, wherein each molecule in the subset includes the pharmacophore; and
(d) deriving one or more new pharmacophores from each new set of data, each new pharmacophore defining a node of the multi-domain classifier.

61. A chemical structure classification method comprising, in combination:
(a) receiving into a computer a set of data representing a training set of molecules, wherein each molecule of the training set has a feature characteristic and an activity characteristic;
(b) using the training set of molecules to generate a chemical structure classifier by a process comprising:
(i) defining groups of the molecules based on similarity of the feature characteristics of the molecules,
(ii) selecting one or more of the groups defined in the preceding step based on the activity characteristics of the molecules in the groups,
(iii) for each group selected in the preceding step, identifying a feature set common to all molecules in the group, and
(iv) for each feature set identified in the preceding step, (A) selecting from the molecules a number of molecules that exhibit the feature set, (B) establishing a new data set consisting of the number of molecules, (C) deciding whether to recursively repeat the method with respect to the new data set, and, if so, (D) repeating steps (i)–(iv) with respect to the molecules represented by the new data set;
(c) applying the chemical structure classifier to classify given molecule into a plurality of structural classes; and
(d) providing as output for presentation to a person an indication of classes into which the given molecule was classified in step (c).

62. A chemical structure classification method as claimed in claim 61,
wherein the chemical structure classifier generated in step (b) comprises a phylogenetic-like tree structure defining a number of nodes beginning with a root node, at least each node after the root node defining a corresponding feature set; and
wherein applying the chemical structure classifier to classify the given molecule comprises filtering the given molecule through the tree structure such that the given molecule passes into a given node of the tree structure if the given molecule contains the feature set defined by the given node.

63. A method as claimed in claim 61, wherein applying the multi-domain chemical structure classifier to classify the given molecule comprises filtering data representative of the given molecule through the multi-domain classifier, the method further comprising providing output data indicative of classifications established by the multi-domain classifier for the given molecule.

64. A method of identifying multiple structural classes into which a given molecule fits comprising, in combination:
representing each of a plurality of molecules by a respective structure characteristic keyed to a set of structural descriptors;
hierarchically clustering representations of the molecules based on their respective structure characteristics, to thereby establish a hierarchical tree structure defining a plurality of nodes, each node representing at least one molecule;
for each of at least a plurality of nodes of the hierarchical tree structure, identifying a respective chemical substructure common to all of the at least one molecule represented by the node, each of at least a plurality of the identified chemical substructures being different than each of the structural descriptors;
filtering a representation of the given molecule through the hierarchical tree structure, the representation of the given molecule thereby falling within a plurality of nodes, wherein, for each given node into which the given molecule falls, the given molecule has the chemical substructure identified for the given node; and
providing as output an indication of the nodes into which the given molecule falls including an indication of the chemical substructure identified for each node into which the given molecule falls,
whereby, each node into which the given molecule falls defines a structural class into which the given molecule fits.

65. A method as claimed in claim 64, wherein the step of identifying a respective chemical substructure for each node of the hierarchical tree is an integral part of the process of hierarchically clustering representations of the molecules to thereby establish the hierarchical tree structure.

66. A method as claimed in claim 64, wherein representing each of a plurality of molecules by a respective structure characteristic keyed to a set of structural descriptors comprises representing each of the molecules in a form selected from the group consisting of (i) a descriptor vector keyed to the structural descriptors and (ii) a 2D graph.

67. A method as claimed in claim 64, wherein hierarchically clustering representations of the molecules based on their respective structure characteristics comprises evaluating similarities between the structure characteristics of the molecules.

68. A method as claimed in claim 67, wherein evaluating similarities between the structure characteristics of the molecules comprises identifying pairs of the molecules and, for each pair, computing a similarity measure between the molecules in the pair.

69. A method as claimed in claim 67, wherein computing the similarity measure comprises computing a measure selected from the group consisting of (i) a Euclidean distance, (ii) a Tanimoto distance, (iii) a Tversky coefficient (iv) a Euclidean-Soergel product, and (v) a Euclidean-Tanimoto product.

70. A method as claimed in claim 64, wherein hierarchically clustering representations of the molecules based on their respective structure characteristics comprises a process selected from the group consisting of (i) divisively clustering the representations and (ii) agglomeratively clustering the representations.

71. A method as claimed in claim 64, wherein each of the structural descriptors is selected from the group consisting of (i) a MACCS key, (ii) a BCI key, and (iii) a Daylight fingerprint key.

72. A software program that implements the method shown in FIG. 2.

* * * * *